(12) United States Patent
Uesaka

(10) Patent No.: US 10,982,148 B2
(45) Date of Patent: Apr. 20, 2021

(54) LIQUID CRYSTAL DEVICE, METHOD FOR PRODUCING SAME, AND COMPOUND

(71) Applicant: JSR CORPORATION, Tokyo (JP)

(72) Inventor: Yuusuke Uesaka, Tokyo (JP)

(73) Assignee: JSR CORPORATION, Tokyo (JP)

( * ) Notice: Subject to any disclaimer, the term of this patent is extended or adjusted under 35 U.S.C. 154(b) by 0 days.

(21) Appl. No.: 16/486,835

(22) PCT Filed: Feb. 2, 2018

(86) PCT No.: PCT/JP2018/003535
§ 371 (c)(1),
(2) Date: Aug. 18, 2019

(87) PCT Pub. No.: WO2018/150906
PCT Pub. Date: Aug. 23, 2018

(65) Prior Publication Data
US 2020/0231875 A1 Jul. 23, 2020

(30) Foreign Application Priority Data

Feb. 20, 2017 (JP) .............................. JP2017-029004

(51) Int. Cl.
*C09K 19/56* (2006.01)
*C07C 69/54* (2006.01)
(Continued)

(52) U.S. Cl.
CPC .............. *C09K 19/56* (2013.01); *C07C 69/54* (2013.01); *C07C 219/34* (2013.01);
(Continued)

(58) Field of Classification Search
CPC ....................... C09K 2323/00; C09K 2323/02; C09K 19/56; C07C 69/54; C07C 219/34;
(Continued)

(56) References Cited

U.S. PATENT DOCUMENTS

2012/0092608 A1* 4/2012 Ito .......................... C09K 19/32
349/183

FOREIGN PATENT DOCUMENTS

JP 2003149647 5/2003
JP 2004123829 A * 4/2004
(Continued)

OTHER PUBLICATIONS

"International Search Report (Form PCT/ISA/210)" of PCT/JP2018/003535, dated Mar. 13, 2018, with English translation thereof, pp. 1-10.

*Primary Examiner* — Ruiyun Zhang
(74) *Attorney, Agent, or Firm* — JCIPRNET

(57) ABSTRACT

This liquid crystal display device is provided with: a pair of substrates which have conductive films, respectively; a liquid crystal layer which is arranged between the pair of substrates and contains a liquid crystal; and a liquid crystal control layer which is formed on the substrate-side interface of the liquid crystal layer by means of polymerization of a polymerizable monomer, and which controls the alignment of the liquid crystal. With respect to this liquid crystal display device, at least one of the pair of substrates is not provided with a liquid crystal alignment film, and the liquid crystal control layer contains a compound that has at least one partial structure which is selected from the group consisting of a fluorene structure-containing group, an aromatic amino group and a nitrogen-containing aromatic heterocyclic group.

18 Claims, 3 Drawing Sheets

(51) Int. Cl.
| | |
|---|---|
| *C07C 219/34* | (2006.01) |
| *C07C 309/46* | (2006.01) |
| *C07D 207/09* | (2006.01) |
| *C07D 209/88* | (2006.01) |
| *C07D 211/26* | (2006.01) |
| *C07D 213/74* | (2006.01) |
| *C07D 239/26* | (2006.01) |
| *C07D 295/096* | (2006.01) |
| *C08G 73/10* | (2006.01) |
| *C08G 77/20* | (2006.01) |
| *G02F 1/1337* | (2006.01) |

(52) U.S. Cl.
CPC .......... *C07C 309/46* (2013.01); *C07D 207/09* (2013.01); *C07D 209/88* (2013.01); *C07D 211/26* (2013.01); *C07D 213/74* (2013.01); *C07D 239/26* (2013.01); *C07D 295/096* (2013.01); *C08G 73/1032* (2013.01); *C08G 73/1042* (2013.01); *C08G 73/1067* (2013.01); *C08G 77/20* (2013.01); *G02F 1/133788* (2013.01); *C09K 2323/00* (2020.08); *C09K 2323/02* (2020.08)

(58) Field of Classification Search
CPC .. C07D 207/09; C07D 209/88; C07D 211/26; C07D 213/74; G02F 1/133788
USPC .................. 428/1.1, 1.2; 349/123, 127, 191; 252/299.4
See application file for complete search history.

(56) References Cited

FOREIGN PATENT DOCUMENTS

| | | |
|---|---|---|
| JP | 5667306 | 2/2015 |
| JP | 2015099170 | 5/2015 |
| JP | 2015099344 | 5/2015 |
| WO | 2010131600 | 11/2010 |
| WO | 2013133082 | 9/2013 |
| WO | 2015033921 | 3/2015 |

* cited by examiner

LIQUID CRYSTAL DEVICE, METHOD FOR PRODUCING SAME, AND COMPOUND

CROSS-REFERENCE TO RELATED APPLICATION

This application is a 371 application of International PCT application serial no. PCT/JP2018/003535, filed on Feb. 02, 2018, which claims the priority benefit of Japanese Patent Application No. 2017-029004, filed on Feb. 20, 2017. The entirety of each of the above-mentioned patent applications is hereby incorporated by reference herein and made a part of this specification.

Technical Field

The present disclosure relates to a liquid crystal device, a method for producing the same, and a compound.

Background Art

Regarding liquid crystal devices, various liquid crystal devices such as vertical alignment (VA) type liquid crystal devices in a vertical (homeotropic) alignment mode using a nematic liquid crystal having negative dielectric anisotropy in addition to a horizontal alignment mode using a nematic liquid crystal having positive dielectric anisotropy represented by a twisted nematic (TN) type or a super twisted nematic (STN) type are known.

In liquid crystal devices, a polymer sustained alignment (PSA) method (for example, refer to Patent Literature 1) is known as one of alignment processing methods. The PSA method is a technology in which a liquid crystal and polymerizable monomers are mixed in advance in a gap between a pair of substrates to constitute liquid crystal cells, and ultraviolet light is then emitted to the liquid crystal cell to polymerize the polymerizable monomers when a voltage is applied between the substrates, and thus a polymer layer is formed at an interface between the liquid crystal layer and the substrate, thereby pretilt angle characteristics being exhibited to control the initial alignment of the liquid crystal. According to this PSA technology, it is possible to increase a viewing angle and speed up a liquid crystal molecule response, and it is possible to solve problems such as insufficient transmittance and contrast which are inevitable in MVA type panels.

In addition, in recent years, a method in which no liquid crystal alignment film is provided on surfaces of a pair of substrates in a PSA method liquid crystal device, and alignment of liquid crystal molecules in the liquid crystal layer is controlled according to a polymer layer formed by polymerizing polymerizable monomers has been proposed (for example, refer to Patent Literature 2 to 4).

CITATION LIST

Patent Literature

[Patent Literature 1]
  Japanese Unexamined Patent Application Publication No. 2003-149647
[Patent Literature 2]
  Japanese Unexamined Patent Application Publication No. 2015-99170
[Patent Literature 3]
  PCT International Publication No. WO 2013/133082
[Patent Literature 4]
  Japanese Patent No. 5667306

SUMMARY OF INVENTION

Technical Problem

A low residual DC is exemplified as one of important characteristics required to improve the quality of a liquid crystal device. A high residual DC causes the occurrence of a so-called "afterimage" in which, when a voltage is turned off after a voltage is applied to a liquid crystal device, an influence of an image that has been displayed previously remains even if the voltage is turned off. In an alignment filmless technology in which control of liquid crystal molecule alignment is performed by a polymer layer formed by polymerizing polymerizable monomers in place of a liquid crystal alignment film, compared to a configuration in which a liquid crystal alignment film is provided, liquid crystal molecule alignment controllability deteriorates and an afterimage (DC afterimage) due to a residual DC tends to easily occur.

In addition, in the alignment filmless technology of the related art, burn-in called "AC afterimage" which is caused when an initial alignment direction gradually shifts according to driving of a liquid crystal device for a long time is likely to occur, and compared to a display device having a liquid crystal alignment film, the quality is currently greatly inferior. In addition, in a liquid crystal device produced by the alignment filmless technology, it is difficult to determine the initial alignment of a liquid crystal and alignment defects are likely to occur immediately after a voltage is applied.

The present disclosure has been made in view of the above problems, and one objective of the present disclosure is to provide a liquid crystal device in which, in a liquid crystal device in which no liquid crystal alignment film is formed on at least one of a pair of substrates, a DC afterimage and an AC afterimage are less likely to occur and initial alignment defects are less likely to occur.

Solution to Problem

In order to address the above problems, the present disclosure provides the following aspects.

[1] A liquid crystal device including a pair of substrates each having a conductive film; a liquid crystal layer which is disposed between the pair of substrates and contains a liquid crystal; and a liquid crystal control layer which is formed at an interface on the side of the substrate of the liquid crystal layer according to polymerization of polymerizable monomers and controls alignment of the liquid crystal, wherein no liquid crystal alignment film is formed on at least one of the pair of substrates, and wherein the liquid crystal control layer contains a compound [A] having at least one partial structure selected from the group consisting of a fluorene structure-containing group, an aromatic amino group and a nitrogen-containing aromatic heterocyclic group.

[2] A method for producing a liquid crystal device which includes a pair of substrates each having a conductive film and in which no liquid crystal alignment film is formed on at least one of the pair of substrates, the method including: Step (I) of constituting a liquid crystal cell by disposing the pair of substrates to face each other with a layer of a liquid crystal composition including a liquid crystal and polymerizable monomers therebetween; and Step (II) of emitting light to the liquid crystal cell when a voltage is applied between the conductive films, wherein the liquid crystal composition contains a compound [B] having at least one partial structure selected from the group consisting of a fluorene structure-containing group, an aromatic amino group and a nitrogen-containing aromatic heterocyclic group.

[3] A compound including at least one selected from the group consisting of a partial structure derived from a compound represented by the following Formula (1), a partial structure derived from a compound represented by the following Formula (2), and a nitrogen-containing aromatic heterocyclic group, and a radically polymerizable group in the same molecule:

[Chem. 1]

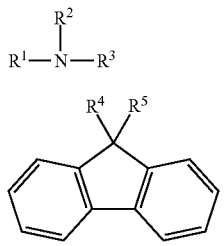

(1)

(2)

(In Formula (1), $R^1$ is a monovalent aromatic ring group, and $R^2$ and $R^3$ are each independently a hydrogen atom or a monovalent organic group having 1 to 30 carbon atoms, and here, $R^2$ and $R^3$ may be mutually bonded to form a ring structure together with the nitrogen atoms to which $R^2$ and $R^3$ are bonded, and $R^1$ and $R^3$ may be mutually bonded to form a nitrogen-containing condensed ring structure including the nitrogen atoms to which $R^1$ and $R^3$ are bonded in the ring. In Formula (2), $R^4$ and $R^5$ are each independently a hydrogen atom or a monovalent organic group having 1 to 30 carbon atoms.)

[4] A compound including at least one selected from the group consisting of a partial structure derived from the compound represented by Formula (1), a partial structure derived from the compound represented by Formula (2), and a nitrogen-containing aromatic heterocyclic group and at least one group selected from the group consisting of an alkoxysilyl group, a hydroxysilyl group, a hydroxyl group, a carboxyl group or salts thereof, a sulfo group or salts thereof, an amino group, a quaternary ammonium base, a phosphate group or salts thereof, a phosphoric acid ester group, a phosphonium base and a carbamoyl group in the same molecule.

Advantageous Effects of Invention

According to the present disclosure, it is possible to provide a liquid crystal device in which a DC afterimage and an AC afterimage are less likely to occur and initial alignment defects are less likely to occur. In addition, it is possible to provide a novel compound using which a liquid crystal device in which a DC afterimage and an AC afterimage are less likely to occur and initial alignment defects are less likely to occur can be obtained.

DESCRIPTION OF EMBODIMENTS

The present embodiment will be described below with reference to the drawings. In the present embodiment, a liquid crystal device is embedded in a liquid crystal display device on which images, characters, and the like are displayed on a display part.

<Liquid Crystal Display Device>

Figure 1:
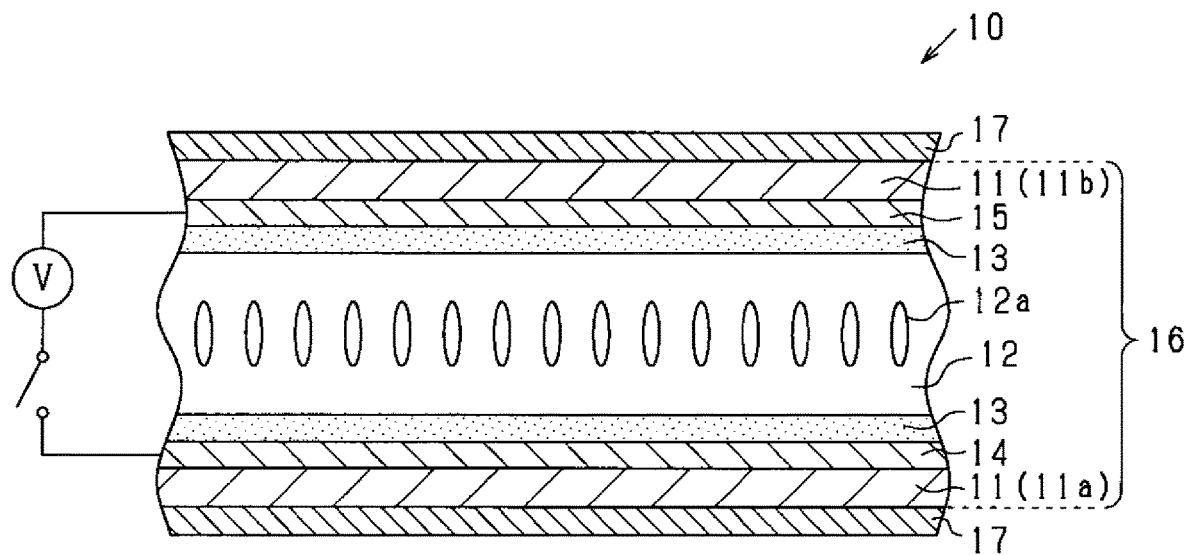
FIG. 1 is a diagram showing a schematic configuration of a liquid crystal display device.

A liquid crystal display device 10 shown in FIG. 1 is a polymer sustained alignment (PSA) type liquid crystal display device including a pair of substrates 11 including a first substrate 11a and a second substrate 11b, and a liquid crystal layer 12 which is disposed between the first substrate 11a and the second substrate 11b. A method for driving the liquid crystal display device 10 is not particularly limited, but in the present embodiment, a thin film transistor (TFT) method is used. Here, a passive matrix method, a plasma addressing method, or the like may be used.

The first substrate 11a and the second substrate 11b have a transparent substrate made of glass, a resin, or the like. For example, in a TFT method color liquid crystal display device, a TFT such as a switching element and various wirings such as a scan line and a signal line are provided on the surface on the side of the liquid crystal layer 12 of one transparent substrate, and a black matrix, a color filter, and the like are provided on the surface on the side of the liquid crystal layer 12 of the other transparent substrate.

The first substrate 11a and the second substrate 11b each have a conductive film which is a transparent electrode made of, for example, indium tin oxide (ITO), on the surface on the side of the liquid crystal layer 12. In the present embodiment, an ITO electrode patterned as a pixel electrode 14 is disposed on the surface of the first substrate 11a, and an ITO electrode not patterned as a common electrode 15 is disposed on the surface of the second substrate 11b. In the liquid crystal display device 10, no liquid crystal alignment film is formed on each surface of the first substrate 11a and the second substrate 11b. Here, in this specification, the "liquid crystal alignment film" refers to an organic film containing a polymer as a main component and having a thickness of 10 nm or more and 300 nm or less. The liquid crystal alignment film is an organic thin film formed by applying a polymer composition in which a polymer such as a polyamic acid and a polyimide is dissolved in an organic solvent to a surface of the substrate on which an electrode is formed.

The first substrate 11a and the second substrate 11b are disposed with a spacer (for example, a columnar spacer or a bead spacer) therebetween with a predetermined gap (cell gap) so that a surface of the first substrate 11a on which an electrode is disposed and a surface of the second substrate 11b on which an electrode is disposed face each other. Peripheral parts of the pair of substrates 11 that are disposed to face each other are bonded via a sealing material (not shown). The liquid crystal layer 12 is formed in a gap surrounded by the first substrate 11a, the second substrate 11b, and the sealing material. The liquid crystal layer 12 is formed using a liquid crystal composition including liquid crystal molecules 12a and polymerizable monomers.

In the liquid crystal layer 12, the liquid crystal control layer 13 that controls alignment of the liquid crystal molecules 12a in the liquid crystal layer 12 is formed at an interface with the pixel electrode 14 on the first substrate 11a and at an interface with the common electrode 15 on the second substrate 11b. The liquid crystal control layer 13 is a layer formed by polymerizing polymerizable monomers that are mixed into the liquid crystal composition in advance after the liquid crystal cell 16 is constituted unlike a liquid crystal alignment film formed on the substrate before a liquid crystal cell 16 is constituted. The liquid crystal control layer 13 contains a compound having at least one partial structure selected from the group consisting of a fluorene structure-containing group, an aromatic amino group and a nitrogen-containing aromatic heterocyclic group.

Here, in this specification, regarding the "compound having at least one partial structure selected from the group consisting of a fluorene structure-containing group, an aromatic amino group and a nitrogen-containing aromatic heterocyclic group," a compound contained in the liquid crystal control layer 13 will be referred to as a "compound [A]" and a compound contained in the liquid crystal composition will be referred to as a "compound [B]." The compound [B] may be a compound that does not change before and after light emission according to a PSA treatment (in this case, the compound [A] and the compound [B] are the same compound) or a compound that is polymerized by light emission (in this case, the compound [A] and the compound [B] are different compounds).

A polarizing plate 17 is disposed outside the first substrate 11a and the second substrate 11b. A terminal area is provided at the outer edge of the first substrate 11a, and a driver IC for driving a liquid crystal and the like are connected to the terminal area, and thus the liquid crystal display device 10 is driven.

<Method for Producing a Liquid Crystal Display Device>

Next, a method for producing the liquid crystal display device 10 will be described. This production method includes the following Step (I) and Step (II).

Step (I): A step of constituting a liquid crystal cell by disposing a pair of substrates having a conductive film to face each other with a layer of a liquid crystal composition including liquid crystal molecules and polymerizable monomers therebetween.

Step (II): A step of emitting light to the liquid crystal cell when a voltage is applied between the conductive films.

The respective steps will be described below in detail.

Step (I)

In order to produce the liquid crystal display device 10 shown in FIG. 1, first, a pair of substrates 11 having a conductive film and having no liquid crystal alignment film (the first substrate 11a and the second substrate 11b) are prepared. A sealing material is applied to a surface of one of the pair of substrates on the side on which an electrode is disposed along the peripheral part of the substrate. Then, in an internal area surrounded by the sealing material on the surface on which an electrode is disposed, a liquid crystal composition including liquid crystal molecules, polymerizable monomers, and the compound [B] is applied by ink jet coating, and a layer of the liquid crystal composition is disposed. Ink jet coating is preferably used because it is then possible to obtain a liquid crystal display device in which initial alignment defects and AC afterimages are further reduced.

Then, the substrate having a layer including the sealing material and the liquid crystal composition is bonded to the other substrate. Thereby, a liquid crystal cell in which a layer of the liquid crystal composition is disposed between the pair of substrates is obtained. In this production method, a process of forming a liquid crystal alignment film on the surfaces of the pair of substrates is not performed.

Here, while the liquid crystal composition is applied by ink jet coating to produce a liquid crystal cell in which a layer of the liquid crystal composition is disposed between the pair of substrates in the above, the method is not limited to ink jet coating. For example, a method in which a liquid crystal composition is added dropwise to a substrate by a one drop filling (ODF) method and then the other substrate is bonded may be used. Alternatively, a method in which peripheral parts of a pair of substrates that are disposed to face each other with a cell gap therebetween are bonded using a sealing material, a liquid crystal composition is injected and filled into a cell gap surrounded by the surface of the substrate and the sealing material and an injection hole is then sealed may be used.

Regarding the liquid crystal cell obtained in Step (I), before light is emitted to the liquid crystal cell in the next Step (II), it is preferable to remove flow alignment when the liquid crystal is filled in by performing an annealing treatment in which cooling to room temperature is slowly performed after heating is performed to a temperature at which the liquid crystal used is brought into an isotropic phase. When such an annealing treatment is performed, liquid crystal alignment properties of the obtained liquid crystal display device can be further improved. In the annealing treatment, the heating temperature is preferably 60° C. to 180° C. and more preferably 80° C. to 150° C. The heating time is preferably 1 minute to 60 minutes, and more preferably 2 minutes to 30 minutes.

This production method may further include a step of applying a silane coupling agent to at least one surface of the pair of substrates having a conductive film before Step (I). This step is preferably included because it is then possible to improve an initial alignment stability and a voltage holding ratio of the obtained liquid crystal display device 10. Regarding the silane coupling agent, a compound having at least one group selected from the group consisting of an alkoxy group and a hydroxyl group and silicon atoms can be preferably used.

Examples of a specific example of the silane coupling agent used include 3-aminopropyltrimethoxysilane, 3-aminopropyltriethoxysilane, 2-aminopropyltrimethoxysilane, 2-aminopropyltriethoxysilane, N-(2-aminoethyl)-3-aminopropyltrimethoxysilane, N-(2-aminoethyl)-3-aminopropylmethyldimethoxysilane, 3-ureidopropyltrimethoxysilane, 3-ureidopropyltriethoxysilane, N-ethoxycarbonyl-3-aminopropyltrimethoxysilane, N-triethoxysilylpropyltriethylenetriamine, 10-trimethoxysilyl-1,4,7-triazadecane, 9-trimethoxysilyl-3,6-diazanonyl acetate, methyl 9-trimethoxysilyl-3,6-diazanonanoate, N-benzyl-3-aminopropyltrimethoxysilane, N-phenyl-3-aminopropyltrimethoxysilane, glycidoxymethyltrimethoxysilane, 2-glycidoxyethyltrimethoxysilane, 3-glycidoxypropyltrimethoxysilane, dimethyloctadecyl [3-(trimethoxysilyl)propyl] ammonium chloride, butyltrialkoxysilane, hexyltrialkoxysilane, octyltrialkoxysilane, octadecyltrialkoxysilane, and hexamethyldisilazane. Here, one type of silane coupling agent may be used alone or two or more thereof may be used in combination.

A method for applying a silane coupling agent to a substrate is not particularly limited, and a method in which a solution in which a silane coupling agent is dissolved in a solvent such as water is prepared, and the prepared solution is applied to a substrate and dried is preferable. The application method is not particularly limited, and examples of the method include an immersion method, a dip method, a spin coating method, a brushing method, and a shower method. A process of applying a silane coupling agent is preferably performed as a part of a washing step for removing foreign substances on the substrate because the operation can then be simplified.

Specifically, first, a silane coupling agent is added to a washing solution (for example, ultra pure water) for the substrate, and the washing solution is applied to at least a surface of the substrate on which an electrode is formed to form a coating film. Here, the washing treatment on the substrate may be performed before or after a spacer is formed. A content of the silane coupling agent in the washing solution is preferably 5 mass % or less, more preferably 0.1 to 2.5 mass %, and most preferably 0.5 to 1 mass %. In consideration of the washing efficiency, a method of immersing a substrate in a washing solution is preferable. The immersion time is, for example, 5 minutes to 2 hours. Then, as necessary, drying is performed by heating or air drying, and thus a substrate on which a thin film including a silane coupling agent is formed can be obtained. Here, the silane coupling agent may be applied to only one substrate of the pair of substrates.

Step (II)

In Step (II), light is emitted to the liquid crystal cell obtained in Step (I). Light emission to the liquid crystal cell may be performed once or may be performed a plurality of times under the same conditions or different conditions. In Step (II), it is preferable to include at least a step of emitting light to a liquid crystal cell when a voltage at which a liquid crystal in the layer of the liquid crystal composition is driven is applied between conductive films so that the liquid crystal control layer 13 formed by light emission stores an initial alignment direction of the liquid crystal molecules 12a.

A voltage to be applied can be, for example, 5 to 50 V DC or AC. Regarding light to be emitted, for example, ultraviolet light and visible light including light with a wavelength of 150 to 800 nm, can be used. However, ultraviolet light including light with a wavelength of 300 to 400 nm is preferable. When the emission light used is linearly polarized or partially polarized light, a light emission direction may be a direction perpendicular to the surface of the substrate, an oblique direction, or a combination thereof. When non-polarized light is emitted, a light emission direction is an oblique direction.

Regarding a light source for emission light, for example, a low pressure mercury lamp, a high pressure mercury lamp, a deuterium lamp, a metal halide lamp, an argon resonance lamp, a xenon lamp, and an excimer laser can be used. Here, ultraviolet light in the above preferable wavelength range can be obtained by a method using a light source in combination with, for example, a diffraction grating filter. A light emission amount is preferably 1,000 to 200,000 $J/m^2$ and more preferably 1,000 to 100,000 $J/m^2$. According to such a light emission treatment, polymerizable monomers in the layer of the liquid crystal composition are polymerized, and the liquid crystal control layer 13 is formed at the interface on the side of the first substrate 11a and at the interface on the side of the second substrate 11b in the liquid crystal layer 12.

Step (II) preferably includes a first step of emitting light to the liquid crystal cell 16 when a voltage lower than a voltage at which the liquid crystal molecules 12a are driven is applied and a second step of emitting light to the liquid crystal cell 16 when a voltage at which the liquid crystal molecules 12a are driven is applied after the first step. When a light emission treatment on the liquid crystal cell is performed in the first step and the second step, it is possible to further improve an initial alignment stability of the liquid crystal molecules 12a. The above description applies to the type of light emitted, a light emission direction, a light emission source and a light emission amount in the first step.

Thus, the liquid crystal display device 10 is obtained by bonding the polarizing plate 17 to the outer surface of the liquid crystal cell. Examples of the polarizing plate 17 include a polarizing plate in which a polarized film called an "H film" in which iodine is absorbed while stretching and aligning a polyvinyl alcohol is inserted into a cellulose acetate protective film and a polarizing plate made of an H film itself.

<Liquid Crystal Composition>

Next, a liquid crystal composition used for forming a liquid crystal layer will be described. The liquid crystal composition includes a liquid crystal (the liquid crystal molecules 12a) and polymerizable monomers. Examples of the liquid crystal include a nematic liquid crystal and a smectic liquid crystal. Among these, a liquid crystal having negative dielectric anisotropy is preferable.

The polymerizable monomer has one, two or more groups that exhibit polymerization due to light, heat, or the like (hereinafter referred to as a "polymerizable group"). The polymerizable group is preferably a radically polymerizable group. Among these, at least one selected from the group consisting of a (meth)acryloyl group, a (meth)acryloyloxy group, a vinyl group, a vinyl phenyl group ($—C_6H_5—CH=CH_2$), a styryl group and an allyl group is particularly preferable. Here, "(meth)acryloyl" in this specification indicates that acryloyl and methacryloyl are included.

A compound having two or more (meth)acryloyl groups is preferably used for the polymerizable monomers. A content of polymerizable monomers is preferably 0.1 to 10.0 mass % and more preferably 0.1 to 5.0 mass % with respect to a total amount of the liquid crystal composition. Here, one type of polymerizable monomers may be used alone or two or more thereof may be used in combination.

(Compound [B])

The liquid crystal composition includes a compound [B] having at least one partial structure selected from the group consisting of a fluorene structure-containing group, an aromatic amino group and a nitrogen-containing aromatic heterocyclic group.

In the compound [B], the aromatic amino group is a group having a structure in which at least one aromatic ring is directly connected to nitrogen atoms, and preferable specific examples include a j-valent group in which j hydrogen atoms are removed from a compound represented by the following Formula (1). In addition, examples of the fluorene structure-containing group include a k-valent group (here, j and k are integers of 1 or more) in which k hydrogen atoms are removed from a compound represented by the following Formula (2).

[Chem. 2]

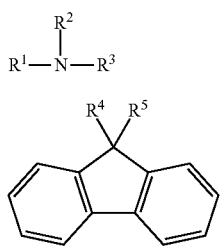

(In Formula (1), $R^1$ is a monovalent aromatic ring group, and $R^2$ and $R^3$ are each independently a hydrogen atom or a monovalent organic group having 1 to 30 carbon atoms, and here, $R^2$ and $R^3$ may be mutually bonded to form a ring structure together with the nitrogen atoms to which $R^2$ and $R^3$ are bonded, and $R^1$ and $R^3$ may be mutually bonded to form a nitrogen-containing condensed ring structure including the nitrogen atoms to which $R^1$ and $R^3$ are bonded in the ring. In Formula (2), $R^4$ and $R^5$ are each independently a hydrogen atom or a monovalent organic group having 1 to 30 carbon atoms.)

In Formula (1), the aromatic ring group in $R^1$ is a group in which one hydrogen atom is removed from a ring part of a substituted or unsubstituted aromatic ring. The aromatic ring includes an aromatic hydrocarbon ring and an aromatic heterocyclic ring, and specific examples thereof include a benzene ring, a naphthalene ring, an anthracene ring, a pyridine ring, a pyrazine ring, a pyrimidine ring, and a pyridazine ring. A benzene ring, a naphthalene ring, a pyridine ring or a pyrazine ring is preferable, and a benzene ring is particularly preferable. Examples of the substituent that an aromatic ring may have include an alkyl group having 1 to 5 carbon atoms and an alkoxy group having 1 to 5 carbon atoms.

Examples of the monovalent organic group for $R^2$ and $R^3$ include a monovalent hydrocarbon group, a group having a hetero atom-containing group between carbon-carbon bonds of the hydrocarbon group, and a heterocyclic group. Here, the term "hydrocarbon group" in this specification refers to chain hydrocarbon groups, alicyclic hydrocarbon groups and aromatic hydrocarbon groups. "Chain hydrocarbon group" refers to linear hydrocarbon groups and branched hydrocarbon groups which do not have a cyclic structure in the main chain and are formed of only a chain structure. Here, the group may be saturated or unsaturated. "Alicyclic hydrocarbon group" refers to hydrocarbon groups having only an alicyclic hydrocarbon structure as a ring structure without an aromatic ring structure. However, the alicyclic hydrocarbon group does not need to be formed of only an alicyclic hydrocarbon structure and it may have a chain structure in a part thereof. "Aromatic hydrocarbon group" refers to hydrocarbon groups having an aromatic ring structure as a ring structure. However, the aromatic hydrocarbon group does not need to be formed of only an aromatic ring structure and it may have a chain structure or an alicyclic hydrocarbon structure in a part thereof. "Hetero atom-containing group" refers to a group having at least one hetero atom, and examples thereof include —O—, —NR—, —CO—O—, —CO—NR—, —CO—, —S—, —$SO_2$—, —Si($CR_3$)$_2$—, —O—Si($CR_3$)$_2$—, and —O—Si($CR_3$)$_2$—O— (R's are each independently a hydrogen atom or a hydrocarbon group having 1 to 10 carbon atoms).

Examples of a ring structure in which $R^2$ and $R^3$ are mutually bonded and which are formed together with nitrogen atoms to which $R^2$ and $R^3$ are bonded include a nitrogen-containing heterocyclic ring such as a piperazine ring, a piperidine ring, and a pyrrolidine ring. In addition, examples of the nitrogen-containing condensed ring structure in which $R^1$ and $R^3$ are mutually bonded and which is formed to include nitrogen atoms to which $R^1$ and $R^3$ are bonded in the ring include a carbazole ring structure.

$R^1$, $R^2$ and $R^3$ are preferably any of the following (a) to (c) because it is then possible to further enhance a DC afterimage reduction effect of the obtained liquid crystal display device 10.

(a) $R^1$ is a monovalent aromatic ring group, $R^2$ is a hydrogen atom or a monovalent hydrocarbon group having 1 to 10 carbon atoms, and $R^3$ is a monovalent aromatic ring group.
(b) $R^1$ is a monovalent aromatic ring group, and $R^2$ and $R^3$ are mutually bonded to form a nitrogen-containing heterocyclic ring.
(c) $R^2$ is a hydrogen atom or a monovalent hydrocarbon group having 1 to 10 carbon atoms, and $R^1$ and $R^3$ are mutually bonded to form a nitrogen-containing condensed ring structure.

In the above (a), $R^2$ is preferably a hydrogen atom, an alkyl group having 1 to 5 carbon atoms, or a substituted or unsubstituted phenyl group. The substituent for the substituted phenyl group is preferably a methyl group or an ethyl group. The above description of $R^1$ applies to the monovalent aromatic ring group for $R^3$. In the above (c), $R^2$ is preferably a hydrogen atom or an alkyl group having 1 to 3 carbon atoms.

Specific examples of the compound represented by Formula (1) include compounds represented by, for example, the following Formula (1-1) to Formula (1-11). Here, the compound [B] may have only one partial structure derived from the compound represented by Formula (1) and may have a total of two or more of the same or different partial structures derived from the compound represented by Formula (1).

[Chem. 3]

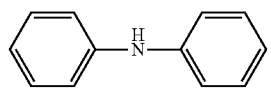
(1-1)

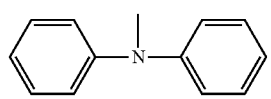
(1-2)

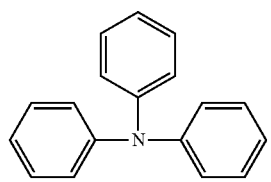
(1-3)

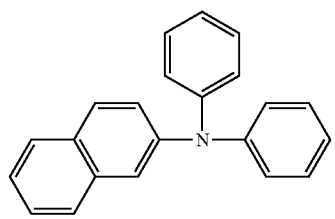
(1-4)

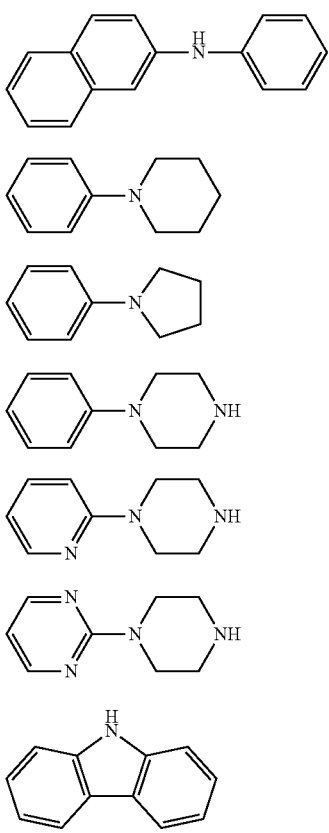

(1-5)

(1-6)

(1-7)

(1-8)

(1-9)

(1-10)

(1-11)

In Formula (2), specific examples of the monovalent organic group for $R^4$ and $R^5$ include groups exemplified as monovalent organic groups for $R^2$ and $R^3$ in Formula (1). Specific examples of the compound represented by Formula (2) include compounds represented by, for example the following Formula (2-1) to Formula (2-4). Here, the compound [B] may have only one partial structure derived from the compound represented by Formula (2) or may have a total of two or more of the same or different partial structures derived from the compound represented by Formula (2).

[Chem. 4]

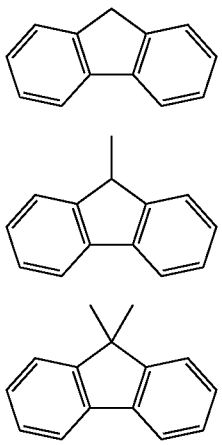

(2-1)

(2-2)

(2-3)

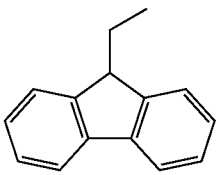

(2-4)

The nitrogen-containing aromatic heterocyclic group is an n-valent group in which n hydrogen atoms are removed from a ring part of a nitrogen-containing aromatic heterocyclic ring. The nitrogen-containing aromatic heterocyclic ring may be an aromatic ring containing one or more nitrogen atoms in the ring framework. Therefore, one, two or more nitrogen atoms may be contained in the ring framework. In addition, only a nitrogen atom may be contained as a hetero atom, or a nitrogen atom and a hetero atom (an oxygen atom, a sulfur atom, etc.) other than a nitrogen atom may be contained.

Specific examples of the nitrogen-containing aromatic heterocyclic ring include, for example, a pyrrole ring, an imidazole ring, a pyrazole ring, a triazole ring, a pyridine ring, a pyrimidine ring, a pyridazine ring, a pyrazine ring, an indole ring, a benzimidazole ring, a purine ring, a quinoline ring, an isoquinoline ring, a naphthyridine ring, a quinoxaline ring, a phthalazine ring, a triazine ring, an azepine ring, a diazepine ring, an acridine ring, a phenazine ring, a phenanthroline ring, an oxazole ring, a thiazole ring, a carbazole ring, a thiadiazole ring, a benzothiazole ring, a phenothiazine ring, and an oxadiazole ring. In the nitrogen-containing aromatic heterocyclic ring, a substituent may be introduced into the ring part. Examples of the substituent include a halogen atom, an alkyl group, and an alkoxy group.

Regarding the nitrogen-containing aromatic heterocyclic ring, among these, a ring framework is preferably a pyrrole ring, an imidazole ring, a pyrazole ring, a triazole ring, a pyridine ring, a pyrimidine ring, a pyridazine ring, a pyrazine ring, a benzimidazole ring, a naphthyridine ring, a phthalazine ring, a quinoxaline ring, a triazine ring, an azepine ring, a diazepine ring or a phenazine ring, and a pyrrole ring, an imidazole ring, a pyrazole ring, a triazole ring, a pyridine ring, a pyrimidine ring, a pyridazine ring or a pyrazine ring is more preferable.

Here, a bonding position for another group in the nitrogen-containing aromatic heterocyclic ring is not particularly limited. For example, when the nitrogen-containing aromatic heterocyclic ring is a 5-membered ring, the bonding position can be the 1-position, the 2-position or the 3-position, and when the nitrogen-containing aromatic heterocyclic ring is a 6-membered ring, the bonding position can be the 1-position, the 2-position, the 3-position or the 4-position. When $R^1$ in Formula (1) is a nitrogen-containing aromatic heterocyclic group, the compound [B] is a compound having an aromatic amino group or a compound having a nitrogen-containing aromatic heterocyclic ring.

The compound [B] may have a long chain alkyl structure having 3 or more carbon atoms because it is then possible to further reduce initial alignment defects of liquid crystal molecules. Examples of the long chain alkyl structure include an alkyl group having 3 to 30 carbon atoms, a fluorine-containing alkyl group having 3 to 30 carbon atoms, an alkoxy group having 3 to 30 carbon atoms, and a fluorine-containing alkoxy group having 3 to 30 carbon atoms, and any of these is preferable. Among these, a group having 5 or more carbon atoms is preferable, and a group having 10 or more carbon atoms is more preferable.

The compound [B] may be a polymerizable monomer or may be a component different from polymerizable monomers. When the compound [B] is a polymerizable monomer, a monomer containing a radically polymerizable group is preferable, and when the compound [B] is a component different from polymerizable monomers, a polar group-containing compound is preferable. The compound [B] is preferably at least one selected from the group consisting of the following (i) and (ii).

(i) A compound [B-1] including at least one selected from the group consisting of a partial structure derived from the compound represented by Formula (1), a partial structure derived from the compound represented by Formula (2), and a nitrogen-containing aromatic heterocyclic group, and a radically polymerizable group in the same molecule.

(ii) A compound [B-2] including at least one selected from the group consisting of a partial structure derived from the compound represented by Formula (1), a partial structure derived from the compound represented by Formula (2), and a nitrogen-containing aromatic heterocyclic group and at least one group (hereinafter referred to as a "polar group E") selected from the group consisting of an alkoxysilyl group, a hydroxysilyl group, a hydroxyl group, a carboxyl group or salts thereof, a sulfo group or salts thereof, an amino group, a quaternary ammonium base, a phosphate group or salts thereof, a phosphoric acid ester group, a phosphonium base and a carbamoyl group in the same molecule.

The radically polymerizable group in the compound [B-1] (hereinafter referred to as a "component b1") is preferably at least one selected from the group consisting of a (meth) acryloyl group, a (meth)acryloyloxy group, a vinyl group, a styrene group and an allyl group, and is more preferably at least one selected from the group consisting of a (meth) acryloyl group and a (meth)acryloyloxy group because it is then highly polymerizable due to light. The number of radically polymerizable groups in the compound [B-1] is preferably 2 or more and more preferably 2 to 4.

The compound [B-1] is preferable because it has a further improved AC afterimage reduction effect in addition to a DC afterimage reduction effect for the obtained liquid crystal display device 10. Specific examples of the compound [B-1] include compounds represented by, for example, the following Formula (b1-1) to Formula (b1-13).

[Chem. 5]

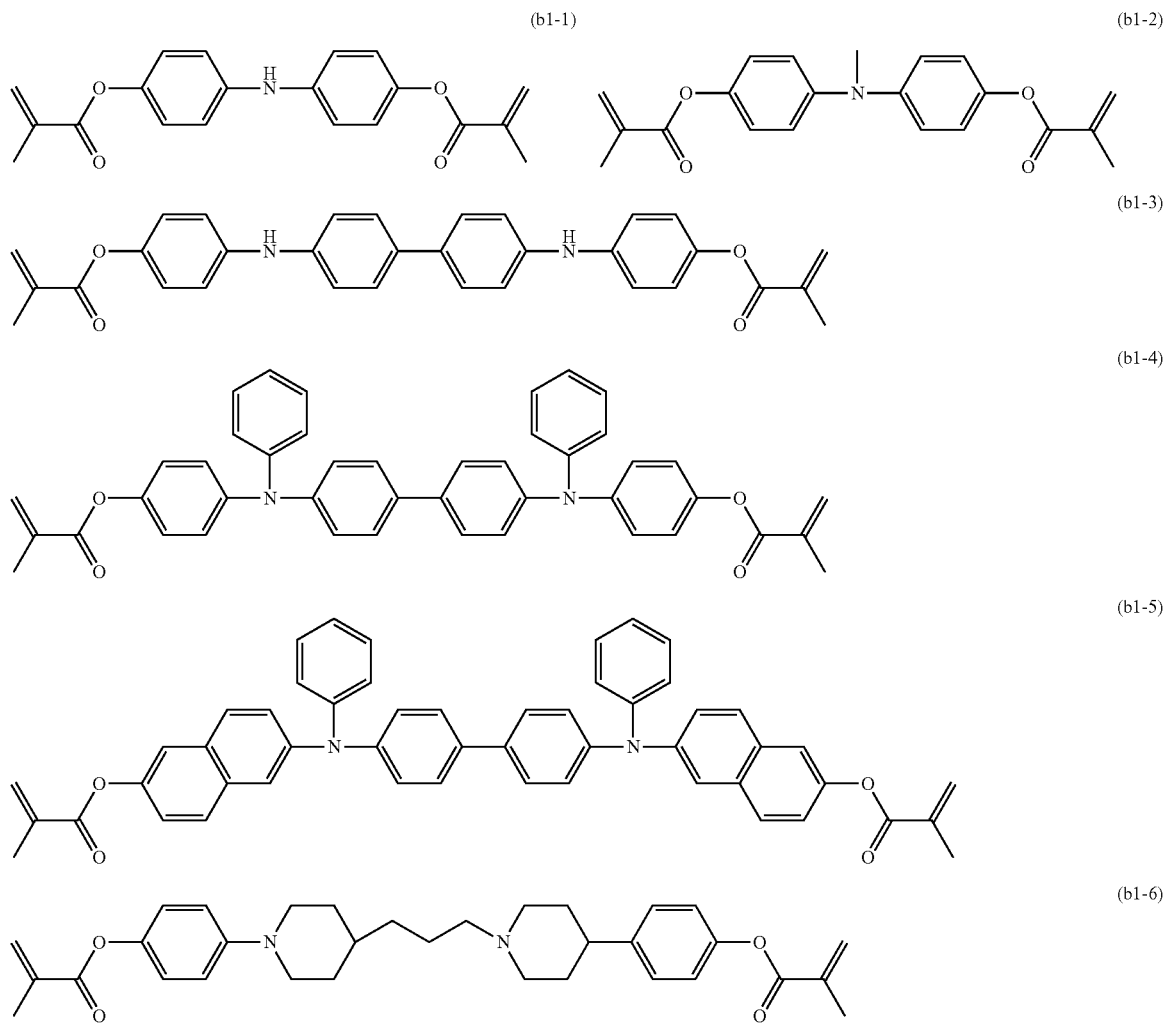

-continued

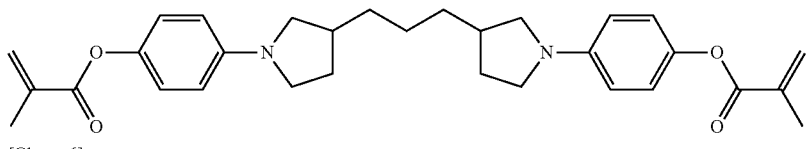

[Chem. 6]

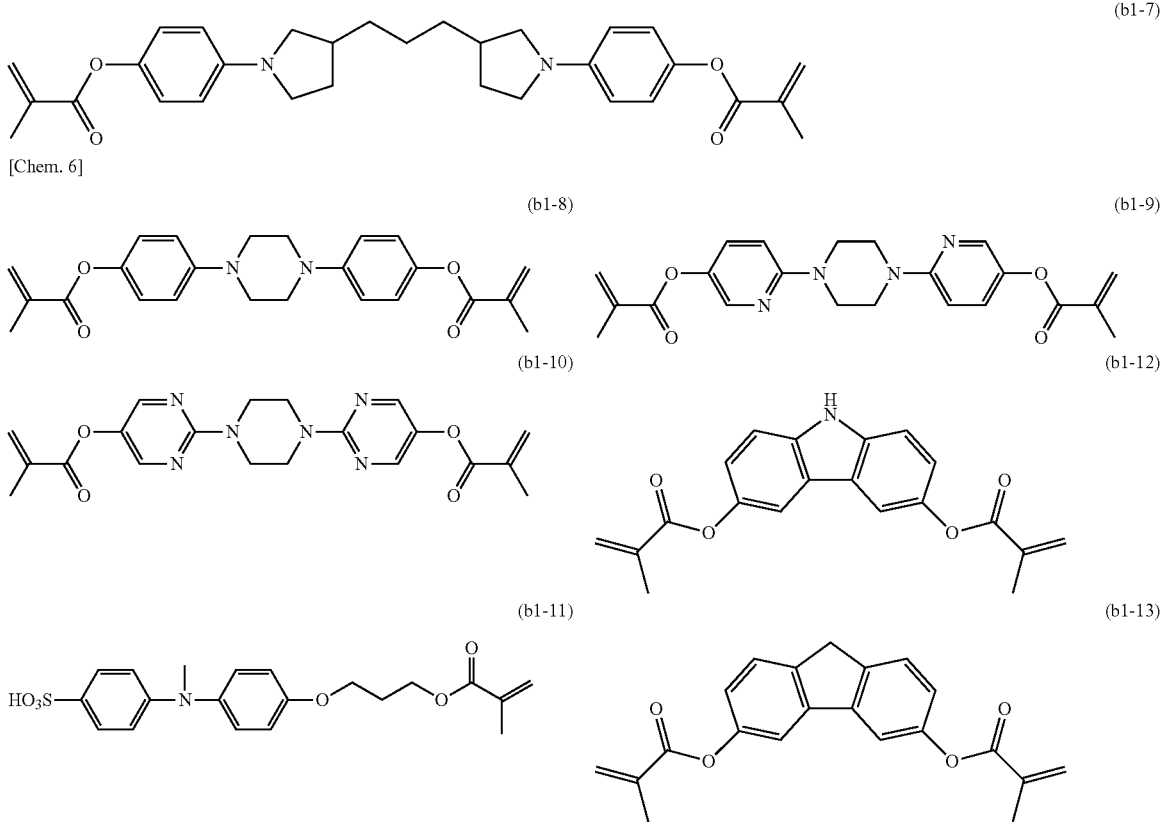

In the compound [B-2] (hereinafter referred to as a "component b2"), the alkoxysilyl group (—SiOR) preferably has 1 to 12 carbon atoms and more preferably has 1 to 6 carbon atoms. The alkoxysilyl group is preferably introduced into the compound [B-2] as a part of a trialkoxysilyl group, a dialkoxyalkylsilyl group or a dialkylalkoxysilyl group.

Among these, the polar group E in the compound [B-2] is preferably at least one selected from the group consisting of an alkoxysilyl group, a hydroxyl group, a carboxyl group or salts thereof, a sulfo group or salts thereof, an amino group, a quaternary ammonium base, a phosphate group or salts thereof, a phosphoric acid ester group, a phosphonium base and a carbamoyl group, and more preferably at least one selected from the group consisting of an alkoxysilyl group, a hydroxyl group, a carboxyl group, a sulfo group, an amino group, a phosphate group, a phosphoric acid ester group and a carbamoyl group.

Here, the compound [B] may have a radically polymerizable group and a polar group E in the same molecule. The compound [B] having a radically polymerizable group and a polar group E in the same molecule corresponds to both the compound [B-1] and the compound [B-2].

The compound [B-2] is preferable because it has a strong effect of reducing initial alignment defects of liquid crystal molecules in addition to a DC afterimage reduction effect for the obtained liquid crystal display device 10. The compound [B-2] is preferably a long chain alkyl structure having 3 or more carbon atoms. Specific examples thereof include, for example, compounds represented by the following Formula (b2-1) to Formula (b2-8) and the compound represented by Formula (b1-11).

[Chem. 7]

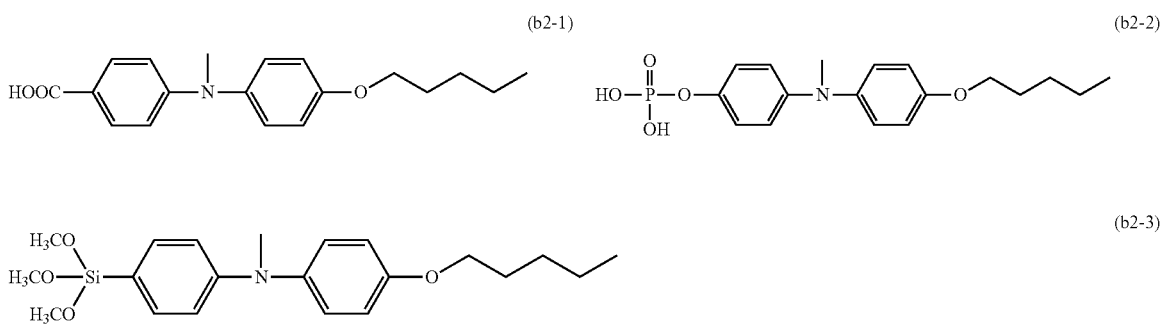

-continued

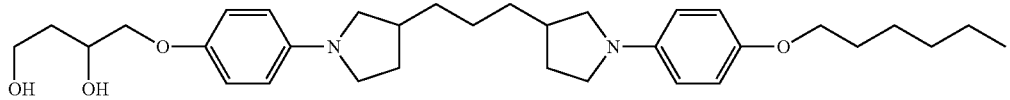
(b2-4)

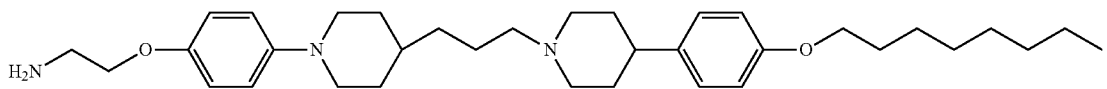
(b2-5)

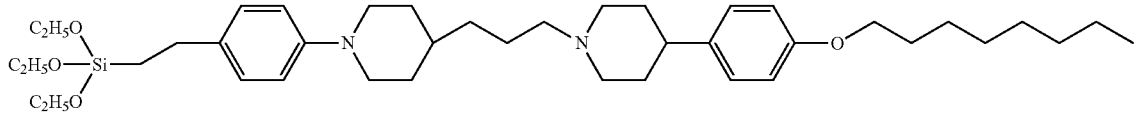
(b2-6)

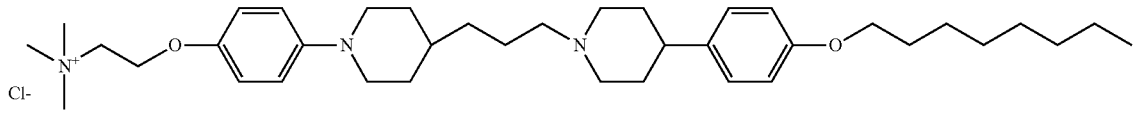
(b2-7)

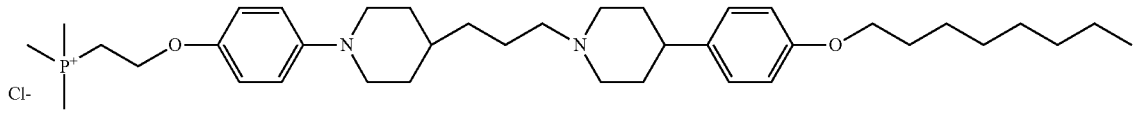
(b2-8)

The compound [B] preferably has at least one selected from the group consisting of a fluorene structure-containing group and an aromatic amino group because a DC afterimage reduction effect of the obtained liquid crystal display device is further improved. Among these, the compound [B] preferably has at least one selected from the group consisting of a partial structure derived from a compound in which at least one of $R^2$ and $R^3$ in Formula (1) is a monovalent aromatic ring group, a partial structure derived from a compound in which $R^1$ and $R^3$ in Formula (1) are mutually bonded to form a nitrogen-containing condensed ring structure including nitrogen atoms to which $R^1$ and $R^3$ are bonded in the ring and a partial structure derived from the compound represented by Formula (2). Here, when a liquid crystal composition containing the compound [B] is used, DC afterimage characteristics of the liquid crystal display device 10 can be improved. One reason for this is speculated to be that, when a component having at least any of a fluorene structure-containing group, an aromatic amino group and a nitrogen-containing aromatic heterocyclic group is contained in the liquid crystal control layer, it is possible to reduce the film resistance of the liquid crystal control layer.

A content of the compound [B] is preferably 0.01 mass % or more and 10 mass % or less with respect to a total amount of the liquid crystal composition because it is then possible to obtain a sufficient DC afterimage reduction effect of the obtained liquid crystal display device 10. The content is more preferably 0.01 mass % or more and 7 mass % or less, and most preferably 0.05 mass % or more and 5 mass % or less. Here, one type of the compound [B] may be used alone or two or more thereof may be used in combination.

When a liquid crystal layer is formed using a liquid crystal composition containing the compound [B], it is possible to obtain a liquid crystal display device in which a compound [A] having at least one partial structure selected from the group consisting of a fluorene structure-containing group, an aromatic amino group and a nitrogen-containing aromatic heterocyclic group is contained in the liquid crystal control layer. Specifically, when a liquid crystal composition containing the compound [B-1] is used, it is possible to obtain a liquid crystal display device in which a polymer of the compound [B-1] as the compound [A] is contained in the liquid crystal control layer. When a liquid crystal composition containing the compound [B-2] is used, it is possible to obtain a liquid crystal display device in which the compound [B-2] as the compound [A] is contained in the liquid crystal control layer.

(Other Polymerizable Monomers)

The liquid crystal composition may contain a compound that does not have any of a partial structure of a fluorene structure-containing group, an aromatic amino group and a nitrogen-containing aromatic heterocyclic group, but has a radically polymerizable group (hereinafter referred to as "other polymerizable monomers"). Regarding the other polymerizable monomers, those known as polymerizable monomers used for producing a PSA type liquid crystal display device can be used. A content of the other polymerizable monomers is preferably adjusted so that a content of polymerizable monomers in the liquid crystal composition is 10 mass % or less. Here, one type of the other polymerizable monomers may be used alone or two or more thereof may be used in combination.

In order to improve various characteristics of the obtained liquid crystal display device, the liquid crystal composition may contain other components shown below in addition to the above components.

(Vertical Alignment Group-Containing Compound)

The liquid crystal composition preferably contains a compound (hereinafter referred to as "compound [C]") having a group that causes liquid crystal molecules to be vertically aligned because it is then possible to further reduce initial alignment defects of liquid crystal molecules in the liquid crystal layer. Preferable specific examples of the vertical alignment group include a partial structure represented by the following Formula (3).

$$*\text{-}L^1\text{-}X^1\text{---}X^2\text{---}X^3\text{---}X^4 \quad (3)$$

(In Formula (3), $L^1$ is —O—, —CO—, —COO—*$^1$, —OCO—*$^1$, —NX$^5$—, —NX$^5$—CO—*$^1$, —CO—NX$^5$—*$^1$, an alkanediyl group having 1 to 6 carbon atoms, —O—X$^6$—*$^1$, or —X$^6$—O—*$^1$ (here, X$^5$ is a hydrogen atom or a monovalent hydrocarbon group having 1 to 10 carbon atoms, and X$^6$ is an alkanediyl group having 1 to 3 carbon atoms, "*$^1$" indicates a bond with X$^1$.)

X$^1$ and X$^3$ are each independently a single bond, a phenylene group or a cycloalkylene group.

X$^2$ is a single bond, a phenylene group, a cycloalkylene group, —X$^7$—B$^1$—*$^2$, or —B$^1$—X$^7$—*$^2$ (here, X$^7$ is a phenylene group or a cycloalkylene group, B$^1$ is a single bond, —COO—*$^3$, —OCO—*$^3$, or an alkanediyl group having 1 to 3 carbon atoms, "*$^2$" indicates a bond with X$^3$, and "*$^3$" indicates a bond with X$^7$).

X$^4$ is a hydrogen atom, a fluorine atom, an alkyl group having 1 to 18 carbon atoms, a fluoroalkyl group having 1 to 18 carbon atoms, an alkoxy group having 1 to 18 carbon atoms, a fluoroalkoxy group having 1 to 18 carbon atoms, or a hydrocarbon group having a steroid structure and having 17 to 51 carbon atoms, and may include a photoinitiator group. Here, when X$^4$ is a hydrogen atom, a fluorine atom or has 1 to 3 carbon atoms, not all of X$^1$, X$^2$ and X$^3$ may be a single bond, "*" indicates a bond.).

Examples of the hydrocarbon group having a steroid structure for X$^4$ and having 17 to 51 carbon atoms include a cholestanyl group, a cholesteryl group, and a lanostanyl group.

The photoinitiator group for X$^4$ is a group having a partial structure derived from a photopolymerization initiator, and is preferably a group having a partial structure derived from a photo-radical polymerization initiator. Regarding specific examples of the photo-radical polymerization initiator, the examples of the photo-radical polymerization initiator in description of the following polymerization initiator can be applied.

Among partial structures represented by Formula (3), the vertical alignment group in the compound [C] is preferably an alkyl group having 7 to 30 carbon atoms, a fluorine-containing alkyl group having 7 to 30 carbon atoms, an alkoxy group having 7 to 30 carbon atoms, a fluorine-containing alkoxy group having 7 to 30 carbon atoms, a group represented by the following Formula (5) or a group having a steroid structure and having 17 to 51 carbon atoms.

[Chem. 8]

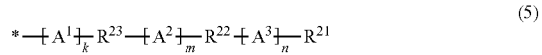

(5)

(In Formula (5), A$^1$ to A$^3$ are each independently a phenylene group or a cyclohexylene group, and may have a substituent in the ring part. R$^{21}$ is a hydrogen atom, an alkyl group having 1 to 20 carbon atoms, an alkoxy group having 1 to 20 carbon atoms, a fluorine-containing alkyl group having 1 to 20 carbon atoms, a fluorine-containing alkoxy group having 1 to 20 carbon atoms or a fluorine atom, and R$^{22}$ and R$^{23}$ are each independently a single bond, —O—, —COO—, —OCO— or an alkanediyl group having 1 to 3 carbon atoms. k, m and n are integers of 0 or more and satisfy 1≤k+m+n≤4. When R$^{21}$ is a hydrogen atom, a fluorine atom or has 1 to 3 carbon atoms, k+m+n≥2 is also satisfied, "*" indicates a bond.)

The compound [C] preferably has at least one of a radically polymerizable group and a polar group E. It is preferable that the compound [C] further include a radically polymerizable group because it is then possible to particularly improve an AC afterimage reduction effect, and it is preferable that the compound [C] further include a polar group E because an effect of reducing initial alignment defects of a liquid crystal is strong. The numbers of radically polymerizable groups and polar groups E in the compound [C] are not particularly limited, and the compound [C] may have one, two or more of only one of the groups, or the compound [C] may have two or more of radically polymerizable groups and polar groups E in total.

Specific examples of the compound [C] include, as a compound having a radically polymerizable group (hereinafter referred to as a "component c1"), for example, compounds represented by the following Formulae (c1-1) to (c1-6), and compounds represented by the following Formulae (c2-1),(c2-3) and (c2-5); and, as a compound having a polar group (hereinafter referred to as a "component c2"), for example, compounds represented by the following Formulae (c2-1) to (c2-10).

[Chem. 9]

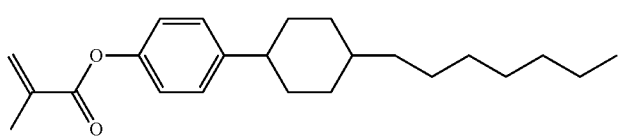

(c1-1)

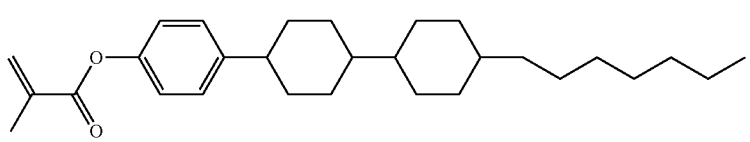

(c1-2)

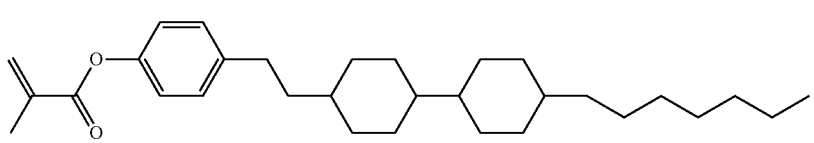

(c1-3)

-continued
(c1-4)
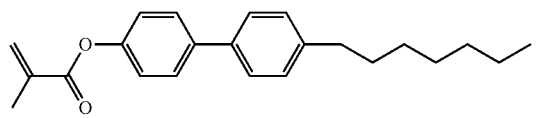
(c1-5)
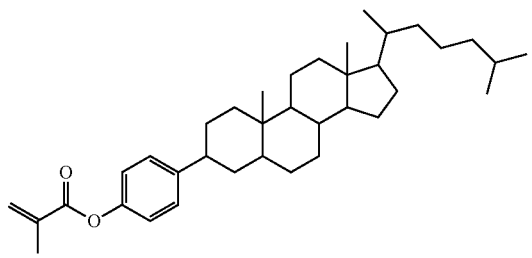
(c1-6)
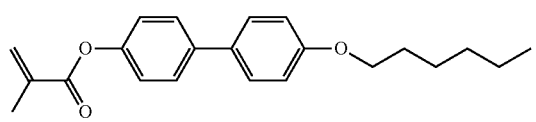
[Chem. 10]
(c2-1)
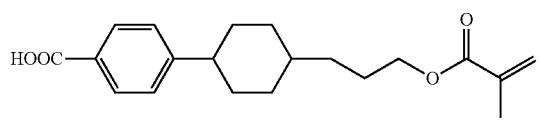
(c2-2)
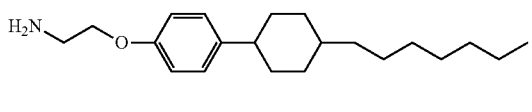
(c2-3)
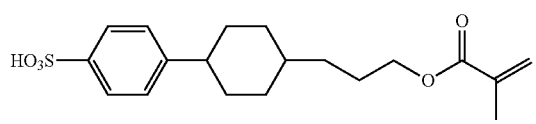
(c2-4)
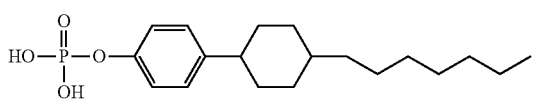
(c2-5)
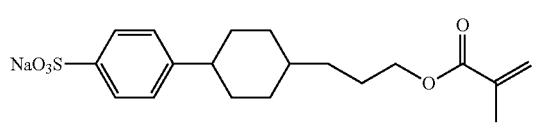
(c2-6)
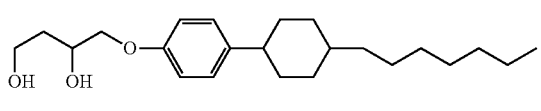
(c2-7)
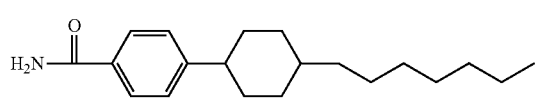
(c2-8)
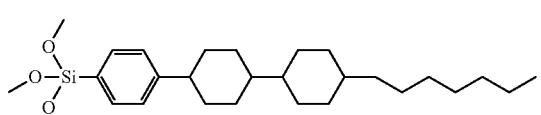
(c2-9)
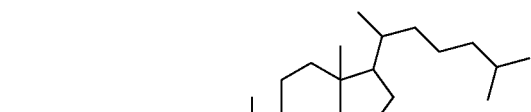
(c2-10)
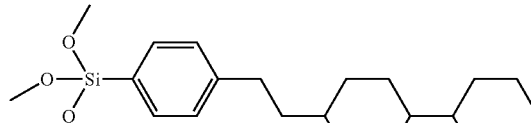

A content of the compound [C] in the liquid crystal composition is preferably 0.01 mass % or more and 7.0 mass % or less with respect to a total amount of the liquid crystal composition. When the content of the compound [C] is set to be within the above range, it is possible to sufficiently improve a response speed and liquid crystal alignment properties of liquid crystal molecules of the obtained liquid crystal display device. The content is more preferably 0.05 mass % or more and 5.0 mass % or less. Here, when the compound [C] has a radically polymerizable group, a content of polymerizable monomers in the liquid crystal composition is preferably 10 mass % or less with respect to a total amount of the liquid crystal composition. One type of the compound [C] may be used alone or two or more thereof may be used in combination.

When the liquid crystal composition further contains the compound [C], the following (1) to (5) forms may be exemplified as preferable forms of combinations of the compound [B] and the compound [C].
(1) A form in which the compound [B] is the component b1 and the compound [C] is the component c1.
(2) A form in which the compound [B] is the component b1 and the component b2, and the compound [C] is the component c2.
(3) A form in which the compound [B] is the component b2 and the compound [C] is the component c2.
(4) A form in which the compound [B] is the component b1 and the compound [C] is the component c2.
(5) A form in which the compound [B] is the component b1 and the compound [C] is the component c1 and the component c2.

Among these, preferably, the component b1 is contained as the compound [B] and the component c2 is contained as the compound [C] because a liquid crystal element in which initial alignment properties of the liquid crystal are excellent and an AC afterimage and a DC afterimage are further reduced is obtained. Specifically, the above (2), (4) and (5) forms are preferable.

The liquid crystal composition preferably contains at least one additive (hereinafter referred to as a "specific additive") selected from the group consisting of a polymerization initiator, a photosensitizer and a polymerization inhibitor because it is then possible to further improve AC afterimage characteristics of the obtained liquid crystal display device. When a liquid crystal composition containing a specific additive is used, the liquid crystal display device 10 in which at least one selected from the group consisting of a polymerization initiator, a sensitizer and a polymerization inhibitor is contained in the liquid crystal control layer 13 is obtained as the liquid crystal display device. Here, one type of specific additive may be used alone or two or more thereof may be used in combination.

(Polymerization Initiator)

Regarding the polymerization initiator, a photo-radical polymerization initiator that generates radicals due to light can be preferably used. Examples of the photo-radical polymerization initiator include an O-acyl oxime compound, an acetophenone compound, and a biimidazole compound.

Regarding specific examples thereof, examples of the O-acyl oxime compound include 1,2-octanedione 1-[4-(phenylthio)-2-(O-benzoyloxime)], ethanone-1-[9-ethyl-6-(2-methylbenzoyl)-9H-carbazole-3-yl]-1-(O-acetyloxime), 1-(9-ethyl-6-benzoyl-9.H.-carbazole-3-yl)-octan-1-one oxime-O-acetate, 1-[9-ethyl-6-(2-methylbenzoyl)-9.H.-carbazole-3-yl]-ethan-1-one oxime-O-benzoate, 1-[9-n-butyl-6-(2-ethylbenzoyl)-9.H.-carbazole-3-yl]-ethan-1-one oxime-O-benzoate, ethanone-1-[9-ethyl-6-(2-methyl-4-tetrahydrofuranylbenzoyl)-9.H.-carbazole-3-yl]-1-(O-acetyloxime), ethanone-1-[9-ethyl-6-(2-methyl-4-tetrahydropyranylbenzoyl)-9.H.-carbazole-3-yl]-1-(O-acetyloxime), and ethanone-1-[9-ethyl-6-(2-methyl-5-tetrahydrofuranylbenzoyl)-9.H.-carbazole-3-yl]-1-(O-acetyloxime), and ethanone-1-[9-ethyl-6-2-methyl-4-(2,2-dimethyl-1,3-dioxolanyemethoxybenzoyl}1-9.H.-carbazole-3-yl]-1-(O-acetyloxime);

examples of the acetophenone compound include α-amino ketone compounds such as 2-benzyl-2-dimethylamino-1-(4-morpholinophenyl)-butan-1-one, 2-dimethylamino-2-(4-methylbenzyl)-1-(4-morpholin-4-yl-phenyl)-butan-1-one, and 2-methyl-1-(4-methylthiophenyl)-2-morpholinopropan-1-one; and α-hydroxy ketone compounds such as 1-phenyl-2-hydroxy-2-methylpropan-1-one, 1-(4-i-propylphenyl)-2-hydroxy-2-methylpropan-1-one, 4-(2-hydroxyethoxy)phenyl-(2-hydroxy-2-propyl)ketone, and 1-hydroxycyclohexyl phenyl ketone; and examples of the biimidazole compound include 2,2'-bis(2-chlorophenyl)-4,4',5,5'-tetraphenyl-1,2'-biimidazole, 2,2'-bis(2,4-dichlorophenyl)-4,4',5,5'-tetraphenyl-1,2'-biimidazole, and 2,2'-bis(2,4,6-trichlorophenyl)-4,4',5,5'-tetraphenyl-1,2'-biimidazole.

Among the above examples, the O-acyl oxime compound is preferably 1,2-octanedione 1-[4-(phenylthio)-2-(O-benzoyloxime)], ethanone-1-[9-ethyl-6-(2-methylbenzoyl)-9H-carbazole-3-yl]-1-(O-acetyloxime), ethanone-1-[9-ethyl-6-(2-methyl-4-tetrahydrofuranylmethoxybenzoyl)-9.H.-carbazole-3-yl]-1-(O-acetyloxime) or ethanone-1-[9-ethyl-6-2-methyl-4-(2,2-dimethyl-1,3-dioxolanyemethoxybenzoyl}-9.H.-carbazole-3-yl]-1-(O-acetyloxime).

The acetophenone compound is preferably an α-amino ketone compound and particularly preferably 2-benzyl-2-dimethylamino-1-(4-morpholinophenyl)-butan-1-one, 2-dimethylamino-2-(4-methylbenzyl)-1-(4-morpholin-4-yl-phenyl)-butan-1-one, or 2-methyl-1-(4-methylthiophenyl)-2-morpholinopropan-1-one.

The biimidazole compound is preferably 2,2'-bis(2,4-dichlorophenyl)-4,4',5,5'-tetraphenyl-1,2'-biimidazole.

A content of the polymerization initiator in the liquid crystal composition is preferably 0.001 mass % or more and 7.0 mass % or less and more preferably 0.001 mass % or more and 5.0 mass % or less with respect to a total amount of the liquid crystal composition. When the content of the polymerization initiator is set to be within the above range, even if an exposure amount during light emission for a PSA treatment is reduced, it is possible to promote polymerization of polymerizable monomers and it is possible to form a liquid crystal control layer having high alignment controllability of liquid crystal molecules. Here, one type of the polymerization initiator may be used alone or two or more thereof may be used in combination.

(Photosensitizer)

The photosensitizer is a compound having a photosensitization function that exhibits a sensitization effect due to light emission. Here, "photosensitization function" refers to a function of rapidly causing intersystem crossing after a singlet excited state begins due to light emission and transitioning the state to a triplet excited state. In the triplet state, when a molecule collides with another molecule, the state of the other molecule is changed to an excited state, and the molecule itself returns to a ground state.

Examples of such a photosensitizer include acetophenone, acetophenone benzyl ketal, 2,2-dimethoxy-2-phenylacetophenone, 3-methylacetophenone, benzophenone, 4-diethylamino-2-hydroxybenzophenone, 2-hydroxybenzophenone, 4-methylbenzophenone, 3,4-dimethylbenzophenone, 3-(4-benzoyl-phenoxy)propyl, 4-chlorobenzophenone, 4,4'-dimethoxybenzophenone, 4,4'-diaminobenzophenone, 4,4'-bis(dimethylamino)benzophenone, benzil, fluoranthene, 3,5-dinitrobenzene, 4-methyl-3,5-dinitrobenzene, anthraquinone, fluorenone, benzaldehyde, fluorene, triphenylamine, carbazole, benzoin propyl ether, 2-acetonaphthone, 1-acetonaphthone, benzoin ethyl ether, thioxanthone, diethylthioxanthone, 2-isopropyl thioxanthone, and 2-chlorothioxanthone.

A content of the photosensitizer is preferably 0.001 mass % or more and 7.0 mass % or less and more preferably 0.001 mass % or more and 5.0 mass % or less with respect to a total amount of the liquid crystal composition. Here, one type of the photosensitizer can be used alone or two or more thereof can be used in combination.

(Polymerization Inhibitor)

For example, the polymerization inhibitor can be used to adjust the sensitivity of the liquid crystal composition with respect to light. Examples of the polymerization inhibitor used include catechols such as phenol, hydroquinone, p-methoxyphenol, benzoquinone, methoxybenzoquinone, 1,2-naphthoquinone, cresol, and p-t-butyl catechol, phenols such as alkyl phenols, alkyl bisphenols, phenothiazine, 2,5-di-t-butylhydroquinone, 2,6-di-t-butylphenol, octadecyl-3-(3,5-di-t-butyl-4-hydroxyphenyl)propionate, N,N'-hexamethylene bis(3,5-di-t-butyl-4-hydroxy-hydrocinnamide), 2,2'-methylene bis(4-methyl-6-t-butylphenol), 4,4'-methylenebis(2,6-di-t-butylphenol), 4,4'-butylidene bis(3-methyl-6-t-butylphenol), 2,6-bis(2'-hydroxy-3'-t-butyl-5'-methylbenzyl)4-methylphenol, 1,1,3-tris(2'-methyl-5'-t-butyl-4'-hydroxyphenyl)butane, 1,3,5-trimethyl-2,4,6-tris(3'-5'-di-t-butyl-4'-hydroxybenzyl)benzene, triethylene glycol bis[3-(3-t-butyl-5-methyl-4-hydroxyphenyl)propionate], pentaerythrityl tetrakis[3-(3,5-di-t-butyl-4-hydroxyphenyl)propionate], 2-t-butyl-6-(3-t-butyl-2-hydroxy-5-methylbenzyl)-4-methylphenyl acrylate, 2,4-dimethyl-6-t-butylphenol and 2-t-butyl-4-methoxyphenol, and at least one of 6-t-butyl-m-cresol, 2,6-di-t-butyl-p-cresol, 2-t-butyl hydroquinone, methylene blue, dimethyldithiocarbamic acid copper salt, diethyldithiocarbamic acid copper salt, dipropyl dithiocarbamic acid copper salt, dibutyldithiocarbamic acid copper salt, copper dibutyl dithiocarbamate, copper salicylate, thiodipropionic acid esters, mercapto benzimidazole, and phosphites. In addition, an oxygen-containing gas such as air may be used in combination.

A proportion of the polymerization inhibitor used is not particularly limited, and, is, for example, is 0.001 mass % or more and 7.0 mass % or less and preferably 0.001 mass % or more and 5.0 mass % or less with respect to a total amount of the liquid crystal composition. One type of the polymerization initiator can be used alone or two or more thereof can be used in combination.

In addition to the above components, other components to be incorporated in the liquid crystal composition include, for example, a chiral agent (for example, product name "C-15", "CB-15" (commercially available from Merck Group)), an antioxidant, a UV absorber, a pigment, and a defoaming agent. These can be appropriately selected and used as long as the effects of the present disclosure are not impaired.

The liquid crystal composition of the present embodiment is prepared by mixing a liquid crystal and polymerizable monomers, and other components to be added as necessary. A process of mixing these components may be performed at room temperature or performed while the temperature is raised. In addition, it is also possible to dissolve the components in an organic solvent (for example, acetone, chloroform, and methanol) and then remove the solvent according to, for example, a distillation operation.

The liquid crystal display device 10 of the present embodiment described in detail above can be effectively applied to various applications, and can be used for various display devices, for example, a clock, a portable game machine, a word processor, a laptop computer, a car navigation system, a camcorder, a PDA, a digital camera, a mobile phone, a smartphone, various monitors, a liquid crystal television, and an information display.

The present disclosure is not limited to the above embodiment, and may be performed, for example, as follows.

The liquid crystal device of the present disclosure may be applied to devices other than the liquid crystal display device. Specifically, for example, it can be applied to a light control device in which a liquid crystal layer is disposed between a pair of substrates (for example, film substrates) having a transparent electrode.

Figure 2:
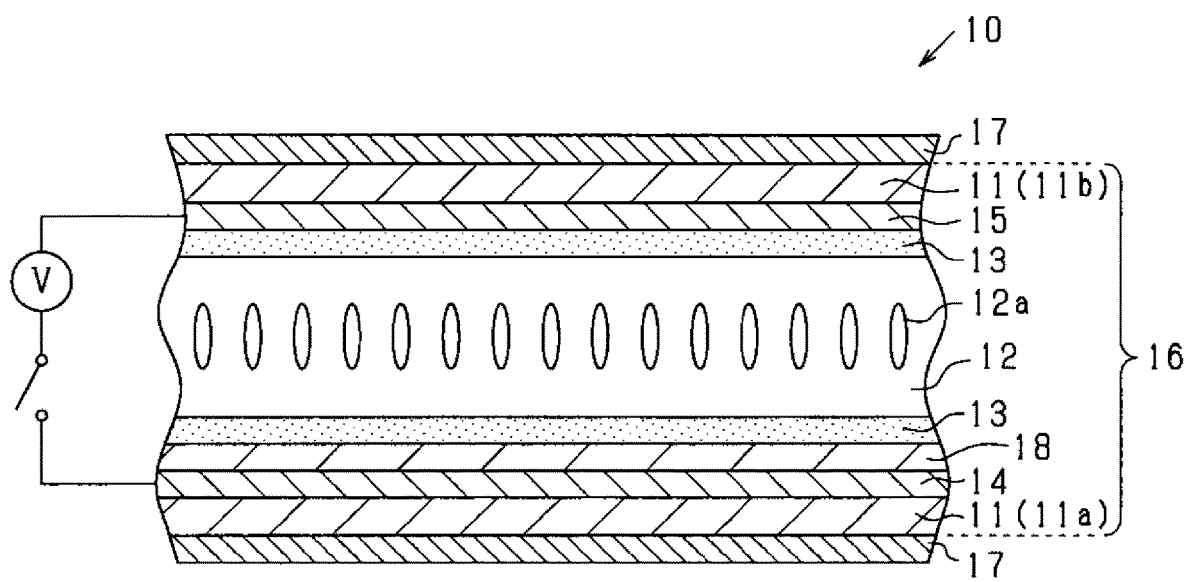
FIG. 2 is a diagram showing a schematic configuration of a liquid crystal display device according to another embodiment.
Figure 3:
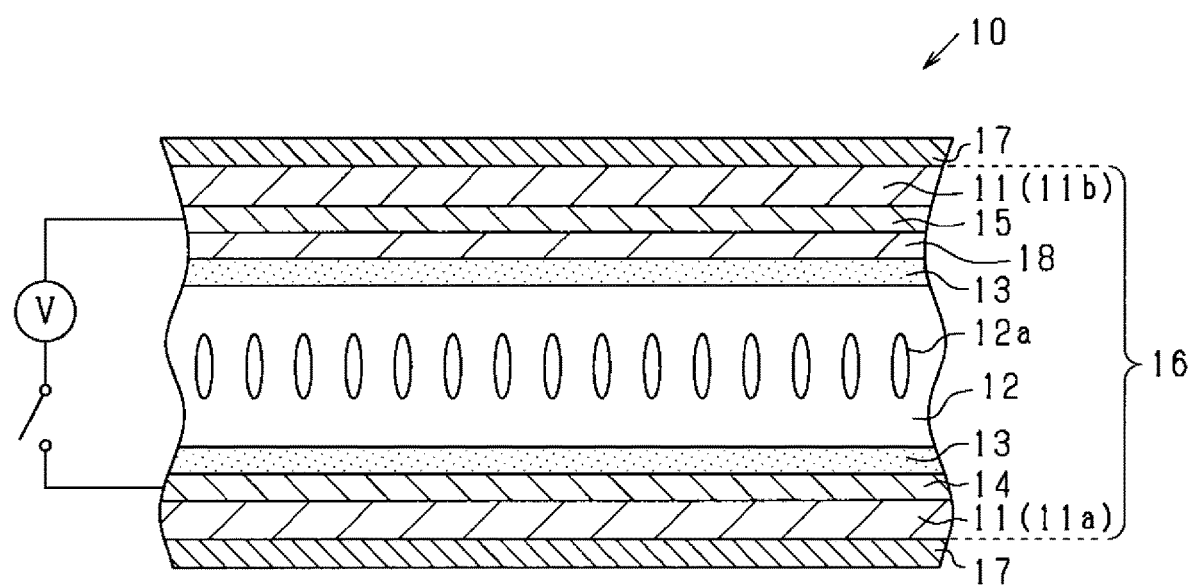
FIG. 3 is a diagram showing a schematic configuration of a liquid crystal display device according to another embodiment.

While a case in which no liquid crystal alignment film is formed on both of the pair of substrates 11 has been described in the above embodiment, a configuration in which a liquid crystal alignment film is formed on one substrate between the pair of substrates and no liquid crystal alignment film is formed on the other substrate may be used. Specifically, as shown in FIG. 2, a configuration in which a liquid crystal alignment film 18 is formed on the pixel electrode 14 of the first substrate 11a between the pair of substrates 11 and no liquid crystal alignment film is formed on the common electrode 15 of the second substrate 11b may be used. In addition, as shown in FIG. 3, a configuration in which the liquid crystal alignment film 18 is formed on the common electrode 15 of the second substrate 11b between the pair of substrates 11 and no liquid crystal alignment film is formed on the pixel electrode 14 of the first substrate 11a may be used.

Examples

While the present disclosure will be described below in further detail with reference to examples, details of the present disclosure are not limited to such examples.

In the following examples and comparative examples, an imidization rate of a polyimide in a polymer solution, a solution viscosity of a polymer solution, a weight average molecular weight of a polymer, and an epoxy equivalent were measured by the following methods.

[Imidization Rate of Polyimide]

A polyimide solution was added to pure water, the obtained precipitate was sufficiently dried at room temperature under a reduced pressure and then dissolved in deuterated dimethyl sulfoxide, and $^1$H-NMR was measured at room temperature using tetramethylsilane as a reference material. An imidization rate [%] was obtained from the obtained $^1$H-NMR spectrum using the following Equation (1).

$$\text{Imidization rate } [\%] = (1 - A^1/A^2 \times \alpha) \times 100 \quad (1)$$

(In Equation (1), $A^1$ is a peak area derived from a proton in an NH group appearing in the vicinity of a chemical shift of 10 ppm, $A^2$ is a peak area derived from other protons, and $\alpha$ is a proportion of the number of other protons with respect to one proton in an NH group in a polymer precursor (polyamic acid).)

[Weight Average Molecular Weight of Polymer]

The weight average molecular weight is a value in terms of polystyrene standards measured through gel permeation chromatography under the following conditions.

Column: TSKgel GRCXLII commercially available from Tosoh Corporation

Solvent: tetrahydrofuran

Temperature: 40° C.

Pressure: 68 kgf/cm$^2$

[Epoxy Equivalent]

The epoxy equivalent was measured by a hydrochloric acid-methyl ethyl ketone method according to JIS C 2105.

Structural formulae of compounds used in this example are shown below. Here, in the following, for convenience of description, "a compound represented by Formula (X)" may be simply referred to as a "compound (X)."

(Tetracarboxylic dianhydride)

[Chem. 11]

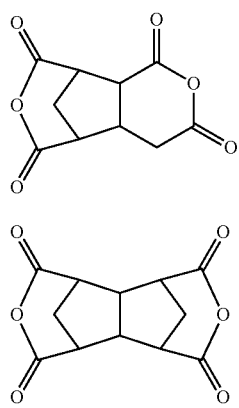

(t-3)

(t-4)

(Diamine)

[Chem. 12]

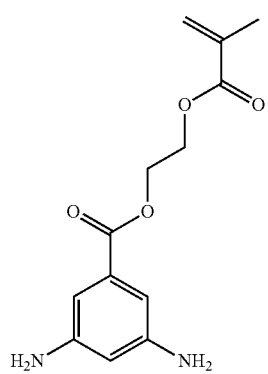

(d-5)

(d-6)

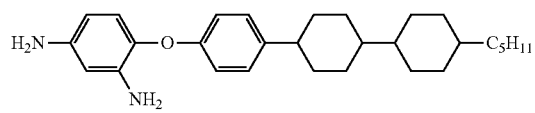

(d-7)

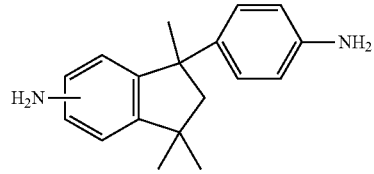

(d-8)

(Silane compound and modified component)

[Chem. 13]

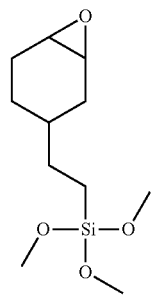

(s-1)

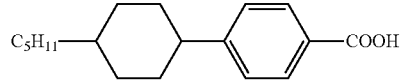

(c-1)

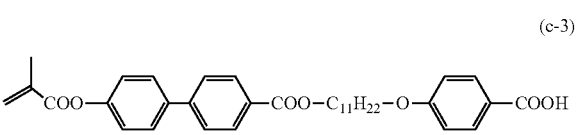

(c-3)

(Other polymerizable monomers)

[Chem. 14]

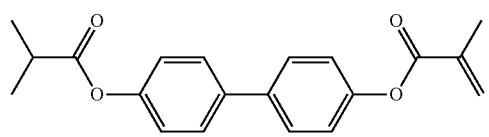

(RM-1)

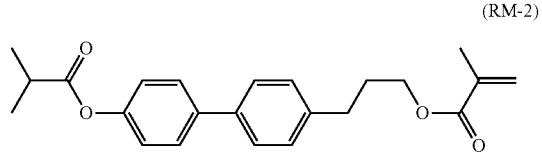

(RM-2)

-continued

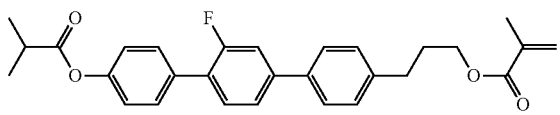

(RM-3)

(Additive)

[Chem. 15]

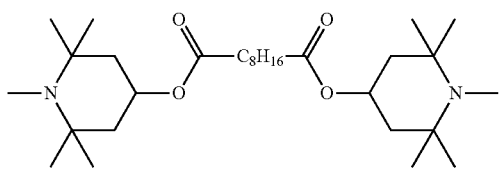

TINUVIN 765
(Inh-1)

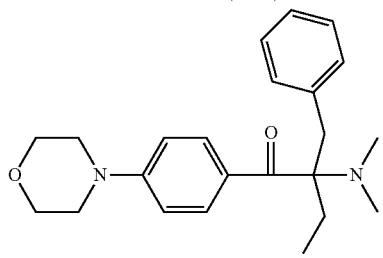

IRGACURE 369E
(Ini-1)

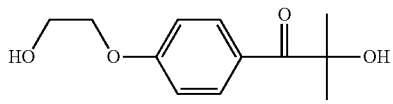

IRGACURE 2959
(Ini-2)

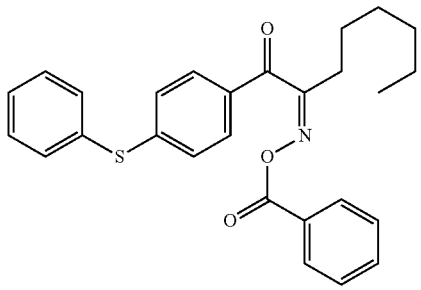

IRGACURE OXE01
(Ini-3)

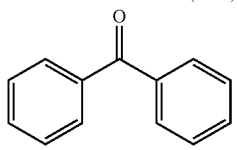

(Sen-1)

<Synthesis of Polymer>
[Synthesis Example 1]

100 parts by mol of a compound (t-3) as a tetracarboxylic dianhydride, 20 parts by mol of a compound (d-6) as a diamine, 50 parts by mol of 3,5-diaminobenzoic acid and 30 parts by mol of a compound (d-8) were dissolved in N-methyl-2-pyrrolidone (NMP), and reacted at room temperature for 6 hours, and thereby a solution containing 20 mass % of a polyamic acid was obtained. Next, pyridine and acetic anhydride were added to the obtained polyamic acid solution and subjected to chemical imidation. The reaction solution after chemical imidation was concentrated and prepared in NMP so that the concentration was 10 mass %. The imidization rate of the obtained polyimide (referred to as a polymer (PI-1)) was about 75%.

[Synthesis Example 2]

100 parts by mol of a compound (t-4) as a tetracarboxylic dianhydride, 30 parts by mol of a compound (d-5) as a diamine, 20 parts by mol of a compound (d-7) and 50 parts by mol of 3,5-diaminobenzoic acid were dissolved in NMP, and reacted at room temperature for 6 hours, and thereby a solution containing 20 mass % of a polyamic acid was obtained. Next, pyridine and acetic anhydride were added to the obtained polyamic acid solution and subjected to chemical imidation. The reaction solution after chemical imidation was concentrated and prepared in NMP so that the concentration was 10 mass %. The imidization rate of the obtained polyimide (referred to as a polymer (PI-2)) was about 80%.

[Synthesis Example 3]

100 g of a compound (s-1), 500 g of methyl isobutyl ketone and 10 g of triethylamine were put into a reaction container including a stirrer, a thermometer, a dropping funnel and a reflux condenser and mixed at room temperature. Next, 100 g of deionized water was added dropwise from the dropping funnel for 30 minutes and reaction was then caused at 80° C. for 6 hours while stirring under reflux. After the reaction was completed, an organic layer was removed, washing was performed with a 0.2 mass % ammonium nitrate aqueous solution so that the water after washing became neutral, the solvent and water were then distilled off under a reduced pressure, and thereby a reactive polyorganosiloxane (ESSQ-1) was obtained as a viscous transparent liquid. When the reactive polyorganosiloxane was subjected to $^1$H-NMR analysis, it was confirmed that a peak based on an epoxy group in the vicinity of chemical shift (δ)=3.2 ppm was obtained, and no side reactions of an epoxy group occurred during the reaction. The weight average molecular weight Mw of the obtained reactive polyorganosiloxane was 3,000, and the epoxy equivalent was 190 g/mol.

[Synthesis Example 4]

10.0 g of a reactive polyorganosiloxane (ESSQ-1), 300 g of methyl isobutyl ketone as a solvent, 3.1 g of a compound (c-1) and 3.1 g of a compound (c-3) as modified components, and 0.10 g of UCAT 18X (product name, commercially available from San-Apro Ltd.) as a catalyst were put into a 500 mL three-neck flask, and reacted at 100° C. for 48 hours under stirring. After the reaction was completed, a solution obtained by adding ethyl acetate to the reaction mixture was washed with water three times, an organic layer was dried using magnesium sulfate, the solvent was then distilled off, and thereby 75 g of a polymerizable group-containing polyorganosiloxane (referred to as a polymer (PSQ-1)) was obtained. The weight average molecular weight Mw of the obtained polymer was 8,000.

<Preparation of Liquid Crystal Composition>
[Preparation Example 1]

0.3 mass % of a compound (RM-1) with respect to a total amount of all constituent components of the liquid crystal composition, 0.1 mass % of a compound represented by Formula (b1-6) with respect to a total amount of all constituent components of the liquid crystal composition, 0.1 mass % of a compound represented by Formula (b1-9) with respect to a total amount of all constituent components of the liquid crystal composition, and 0.3 mass % of a compound represented by Formula (c1-1) with respect to a total amount of all constituent components of the liquid crystal composition were added to 10 g of a nematic liquid crystal (MLC-6608 commercially available from Merck Group), and these were mixed together, and thereby a liquid crystal composition (LC-1) was obtained.

[Preparation Examples 2 to 13]

Figure 4:
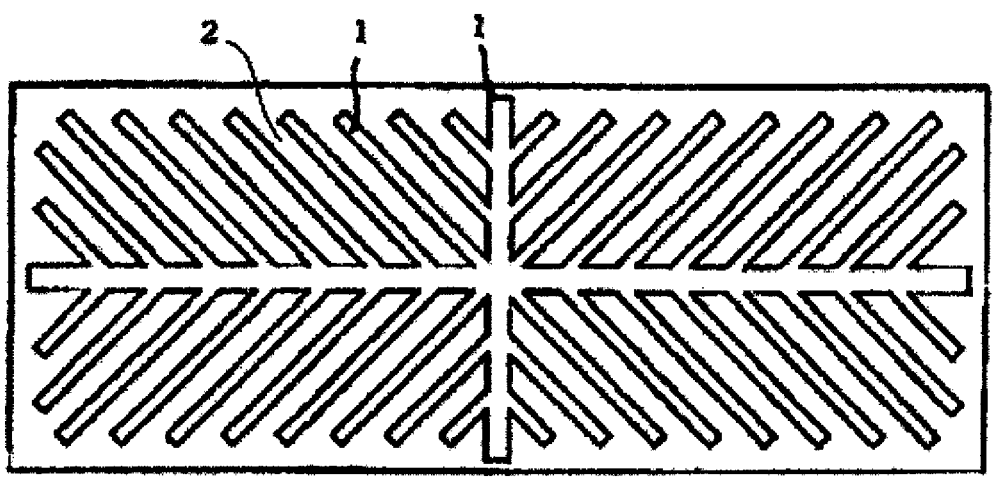
FIG. 4 is a diagram showing a pattern of a transparent conductive film of a liquid crystal cell used in an example.
Figure 5:
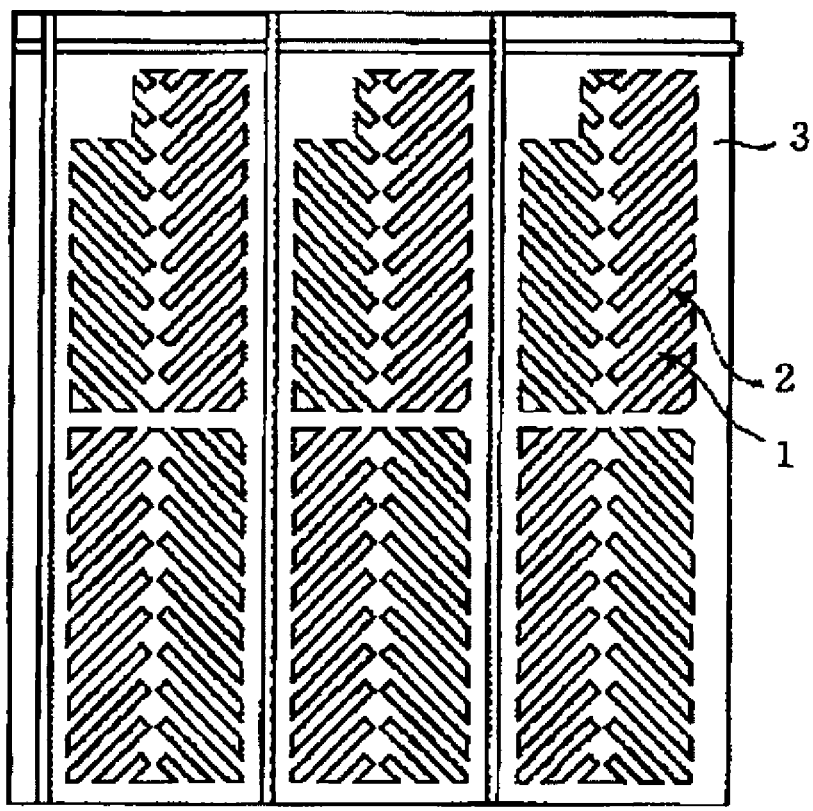
FIG. 5 is a diagram showing a pattern of a transparent conductive film of a liquid crystal cell used in an example.

Liquid crystal compositions (LC-2) to (LC-10) and (LC-R1) to (LC-R3) were prepared in the same manner as in Preparation Example 1 except that the types and amounts of compounds added to 10 g of a nematic liquid crystal (MLC-6608 commercially available from Merck Group) were changed as in the following Table 1. Here, in Table 1, numerical values in the parentheses indicate proportions of compounds used [mass %] with respect to a total amount of the liquid crystal composition. The abbreviations of the compound [B] and the compound [C] in Table 1 correspond to reference numerals in the parentheses denoting the compounds exemplified above.

a glass substrate having an ITO electrode with no pattern, and in which a 3.5 μm column spacer was provided on the surface on the side of the electrode of the glass substrate having an ITO electrode with no pattern between these substrates was prepared. In this example, a fishbone-like electrode pattern of line/space=3.5 μm/3.5 μm was formed. The electrode patterns of the patterned ITO electrode used here are shown in FIG. 4 and FIG. 5, whereby the ITO electrode 1, the slit part 2 and a light shielding film 3 are illustrated. In addition, regarding the electrode, two ITO electrodes (an electrode A and an electrode B) that could individually switch between application and no application of a voltage were used.

Next, an epoxy resin adhesive containing aluminum oxide spheres with a diameter of 3.5 μm was applied to the outer edge of the ITO surface of the glass substrate having the patterned ITO electrode and the liquid crystal composition (LC-1) was then added dropwise at 6 points (2 points in a vertical direction×3 points in a horizontal direction and a distance between the points being 10 mm in the vertical and

TABLE 1

| | Liquid crystal composition | Base crystal | Other polymerizable monomers | Compound [B] Component b1 | Compound [B] Component b2 | Compound [C] Component c1 | Compound [C] Component c2 | Additive |
|---|---|---|---|---|---|---|---|---|
| Preparation Example 1 | LC-1 | MLC-6608 | RM-1 (0.3) | b1-6 (0.1) b1-8 (0.1) | | c1-1 (0.3) | | |
| Preparation Example 2 | LC-2 | MLC-6608 | RM-1 (0.3) | b1-9 (0.5) | | c1-2 (0.3) | | Inh-1 (0.05) |
| Preparation Example 3 | LC-3 | MLC-6608 | RM-1 (0.3) | b1-3 (0.7) | | c1-3 (0.3) | c2-1 (0.3) | Inh-1 (0.1) |
| Preparation Example 4 | LC-4 | MLC-6608 | RM-2 (0.3) | b1-12 (1.0) | | | c2-2 (0.3) | Sen-1 (0.1) |
| Preparation Example 5 | LC-5 | MLC-6608 | RM-2 (0.3) | b1-13 (1.0) | b2-1 (0.5) | | c2-3 (0.5) | Sen-1 (0.2) |
| Preparation Example 6 | LC-6 | MLC-6608 | RM-2 (0.3) | | b2-2 (0.5) | | c2-6 (0.5) | Ini-1 (0.1) |
| Preparation Example 7 | LC-7 | MLC-6608 | RM-3 (0.3) | | b2-4 (0.5) | | c2-7 (0.8) | Ini-1 (0.3) |
| Preparation Example 8 | LC-8 | MLC-6608 | RM-3 (0.3) | b1-12 (1.2) | b2-5 (0.5) | | c2-8 (0.8) | Ini-2 (0.3) |
| Preparation Example 9 | LC-9 | MLC-6608 | RM-3 (0.3) | b1-13 (1.2) | b2-6 (0.5) | | c2-9 (1.0) | Ini-2 (0.5) |
| Preparation Example 10 | LC-10 | MLC-6608 | RM-3 (0.3) | b1-12 (0.5) b1-13 (1.0) | | | c2-7 (0.6) c2-10 (0.6) | Ini-3 (0.5) |
| Preparation Example 11 | LC-R1 | MLC-6608 | RM-1 (2.0) | | | | | |
| Preparation Example 12 | LC-R2 | MLC-6608 | RM-1 (2.0) | | | | | Ini-1 (0.1) |
| Preparation Example 13 | LC-R3 | MLC-6608 | RM-2 (1.0) | | | c1-1 (0.3) | c2-1 (0.3) | Ini-1 (0.1) |

<Preparation of Liquid Crystal Alignment Agent>
[Preparation Example 14]

The polymer (PSQ-1) was added to a solution containing the polymer (PI-1) as a polymer component so that polymer (PI-1):polymer (PSQ-1)=95:5 (mass ratio), and NMP and butyl cellosolve (BC) were additionally added as solvents, and sufficiently stirred and a solution having a solvent composition of NMP:BC=50:50 (mass ratio) and a solid content concentration of 6.5 mass % was obtained. The solution was filtered using a filter with a pore size of 1 μm and thereby a liquid crystal alignment agent (AL-1) was prepared.

[Preparation Example 15]

NMP and BC were added to a solution containing the polymer (PI-2) as a polymer component, and sufficiently stirred, and a solution having a solvent composition of NMP:BC=50:50 (mass ratio) and a solid content concentration of 6.5 mass % was obtained. The solution was filtered using a filter with a pore size of 1 μm and thereby a liquid crystal alignment agent (AL-2) was prepared.

<Production and Evaluation of Liquid Crystal Device>
[Example 1]
[Production of Liquid Crystal Display Element]

A pair of substrates which included a glass substrate having an ITO electrode patterned in a fishbone shape and horizontal directions, and a coating amount at each point being 0.6 mg) on the inner surface of the epoxy resin adhesive. The substrate and another glass substrate were superimposed so that they faced each other and were compressed, and the adhesive was cured to produce a liquid crystal cell. The obtained liquid crystal cell was subjected to ultraviolet light emission and annealing according to a "PSA process-1" to be described below, and thereby a liquid crystal cell for evaluation was produced.

[Evaluation of alignment properties]

The liquid crystal cell for evaluation was observed under a polarizing microscope when polarizing plates were disposed orthogonally, and the number of alignment defects in the plane was counted. In this case, when the number of alignment defects was 0, alignment properties were evaluated as "very favorable (⊚)," when the number of alignment defects was 1 or more and less than 6, alignment properties were evaluated as "favorable (○)," when the number of alignment defects was 6 or more and less than 11, alignment properties were evaluated as "acceptable (Δ)," and when the number of alignment defects was 11 or more, alignment properties were evaluated as "poor (×)." The results in this example were that the number of alignment defects was 10 and alignment properties were evaluated as "acceptable (Δ)."

[Evaluation of Afterimage Characteristics (AC Afterimage Evaluation)]

The liquid crystal cell for evaluation was left at 60° C., no voltage was applied to the electrode B, and an AC voltage of 10 V was applied to the electrode A for 300 hours. Immediately after 300 hours, an AC voltage of 3 V was applied to both the electrode A and the electrode B, and a difference ΔT [%] between light transmittances of both electrodes was measured. In this case, when ΔT was less than 1%, AC afterimage characteristics were evaluated as "very favorable (⊚)," when ΔT was 1% or more and less than 2%, AC afterimage characteristics were evaluated as " favorable (○)," when ΔT was 2% or more and less than 3%, AC afterimage characteristics were evaluated as "acceptable (Δ)," and when ΔT was 3% or more, AC afterimage characteristics were evaluated as "poor (×)." The results of Example 1 were that ΔT was 2.6% and AC afterimage characteristics were evaluated as "acceptable (Δ)."

[Evaluation of Afterimage Characteristics (DC Afterimage Evaluation)]

The liquid crystal cell for evaluation was left at 60° C., a DC voltage of 0.5 V was applied to the electrode A for 24 hours, and a voltage (residual DC voltage) remaining on the electrode A immediately after the DC voltage was cut off was determined by a flicker elimination method. In this case, when the residual DC voltage was less than 50 mV, DC afterimage characteristics were evaluated as "very favorable (⊚)," when the residual DC voltage was 50 mV or more and less than 100 mV, DC afterimage characteristics were evaluated as "favorable (○)," when the residual DC voltage was 100 mV or more and less than 300 mV, DC afterimage characteristics were evaluated as "acceptable (Δ)," and when the residual DC voltage was 300 mV or more, DC afterimage characteristics were evaluated as "poor (×)." The results of Example 1 were that the residual DC voltage was 200 mV and DC afterimage characteristics were evaluated as "acceptable (Δ)."

[Examples 2 to 5 and Comparative Examples 1 and 2]

Liquid crystal cells for evaluation were produced in the same manner as in Example 1 except that the type of the liquid crystal composition used was changed as in the following Table 2 and the PSA process performed when the liquid crystal cell for evaluation was produced was changed as in the following Table 2. Then, the obtained liquid crystal cell for evaluation was evaluated in the same manner as in Example 1. The results are shown in the following Table 2.

[Example 6]

A liquid crystal cell for evaluation was produced in the same manner as in Example 1 except that the type of the liquid crystal composition used was changed as in the following Table 2, the liquid crystal was applied by an inkjet method (a coating amount per droplet was 600 pg), and the PSA process performed when the liquid crystal cell for evaluation was produced was changed to a "PSA process-3" shown below. Then, the obtained liquid crystal cell for evaluation was evaluated in the same manner as in Example 1. The results are shown in the following Table 2.

[Examples 7 and 8 and Comparative Example 3]

Liquid crystal cells for evaluation were produced in the same manner as in Example 6 except that the type of the liquid crystal composition used was changed as in the following Table 2, and the PSA process performed when the liquid crystal cell for evaluation was produced was changed as in the following Table 2. Then, the obtained liquid crystal cell for evaluation was evaluated in the same manner as in Example 1.

The results are shown in the following Table 2.

[Example 9]

A pair of substrates which included a glass substrate having an ITO electrode (pixel electrode) patterned in a fishbone shape and a glass substrate having an ITO electrode (common electrode) with no pattern, and in which a 3.5 μm column spacer was provided on the surface on the side of the electrode of the glass substrate having a common electrode between these substrates was prepared. The liquid crystal alignment agent (AL-1) prepared above was applied to the surface of the ITO electrode of the glass substrate having a patterned ITO electrode between the substrates using a liquid crystal alignment film printer. Next, heating (pre baking) was performed on a hot plate at 80° C. for 1 minute, the solvent was removed, and heating (post baking) was then performed on a hot plate at 230° C. for 15 minutes, and a coating film with an average film thickness of 100 nm (liquid crystal alignment film) was formed. Next, the surface of the ITO electrode of the glass substrate having an ITO electrode with no pattern was treated with 3-aminopropyltriethoxysilane.

Then, a liquid crystal cell for evaluation was produced in the same manner as in Example 6 except that the type of the liquid crystal composition used was changed to a liquid crystal composition (LC-9) and the PSA process performed when the liquid crystal cell for evaluation was produced was changed to a "PSA process-4." Then, the obtained liquid crystal cell for evaluation was evaluated in the same manner as in Example 1. The results are shown in the following Table 2.

[Example 10]

A liquid crystal cell for evaluation was produced in the same manner as in Example 9 except that, in Example 9, octyltrimethoxysilane was used in place of 3-aminopropyltriethoxysilane and the liquid crystal alignment agent (AL-2) was used in place of the liquid crystal alignment agent (AL-1). Then, the obtained liquid crystal cell for evaluation was evaluated in the same manner as in Example 1. The results are shown in the following Table 2.

TABLE 2

| | Treatment of surface of substrate (Non-pattern substrate) | Alignment film (Pattern substrate) | Type of liquid crystal composition | Method of applying liquid crystal composition | Type of PSA process | Alignment properties | | Light transmittance | | DC afterimage | |
|---|---|---|---|---|---|---|---|---|---|---|---|
| | | | | | | Determination | defects [number] | Determination | AC afterimage difference ΔT [%] | Determination | Residual DC [mV] |
| Example 1 | None | None | LC-1 | Drop | PSA-1 | Δ | 10 | Δ | 2.6 | Δ | 200 |
| Example 2 | None | None | LC-2 | Drop | PSA-1 | Δ | 8 | Δ | 2.2 | Δ | 250 |
| Example 3 | None | None | LC-3 | Drop | PSA-2 | ○ | 5 | Δ | 2.1 | ○ | 90 |

TABLE 2-continued

| | Treatment of surface of substrate (Non-pattern substrate) | Alignment film (Pattern substrate) | Type of liquid crystal composition | Method of applying liquid crystal composition | Type of PSA process | Evaluation results | | | | | |
|---|---|---|---|---|---|---|---|---|---|---|---|
| | | | | | | Alignment properties | | AC afterimage | | DC afterimage | |
| | | | | | | | | Light trans-mittance | | | |
| | | | | | | Alignment | | | | | |
| | | | | | | Determination | defects [number] | Determination | difference ΔT [%] | Determination | Residual DC [mV] |
| Example 4 | None | None | LC-4 | Drop | PSA-2 | ○ | 4 | ○ | 1.8 | ○ | 70 |
| Example 5 | None | None | LC-5 | Drop | PSA-3 | ○ | 3 | ○ | 1.5 | ○ | 80 |
| Example 6 | None | None | LC-6 | Inkjet | PSA-3 | ⊚ | 0 | ⊚ | 0.8 | ○ | 80 |
| Example 7 | None | None | LC-7 | Inkjet | PSA-3 | ⊚ | 0 | ⊚ | 0.7 | Δ | 70 |
| Example 8 | None | None | LC-8 | Inkjet | PSA-4 | ⊚ | 0 | ⊚ | 0.8 | ⊚ | 30 |
| Example 9 | APTES | AL-1 | LC-9 | Inkjet | PSA-4 | ⊚ | 0 | ⊚ | 0.6 | ⊚ | 30 |
| Example 10 | OTMS | AL-2 | LC-10 | Inkjet | PSA-4 | ⊚ | 0 | ⊚ | 0.5 | ⊚ | 20 |
| Comparative Example 1 | None | None | LC-R1 | Drop | PSA-1 | X | 16 | X | 3.6 | X | 360 |
| Comparative Example 2 | None | None | LC-R2 | Drop | PSA-2 | X | 14 | Δ | 2.9 | X | 320 |
| Comparative Example 3 | None | None | LC-R3 | Inkjet | PSA-4 | ○ | 5 | ○ | 0.8 | X | 370 |

In Table 2, "APTES" means that the surface of the substrate was treated with 3-aminopropyltriethoxysilane and "OTMS" means that the surface of the substrate was treated with octyltrimethoxysilane.

<PSA Process>

Details of the "PSA process-1" to "PSA process-4" performed in Examples 1 to 10 and Comparative Examples 1 to 3 are as follows.

(PSA Process-1)

For the liquid crystal cell, an AC of 20 Vpp with a frequency of 60 Hz was applied between the electrodes, and when the liquid crystal was driven, ultraviolet light of 80 mW was emitted for 50 seconds using a UV irradiation device using a metal halide lamp as a light source. Subsequently, when no voltage was applied, ultraviolet light of 3.5 mW was emitted for 30 minutes using a UV irradiation device using a metal halide lamp as a light source. Finally, the liquid crystal cell was annealed in a clean oven at 120° C. for 10 minutes. In addition, an emission amount here was a value determined using a light meter measured based on a wavelength of 365 nm (similarly applies to the PSA process-2 to PSA process-4).

(PSA Process-2)

For the liquid crystal cell, an AC of 30 Vpp with a frequency of 60 Hz was applied between the electrodes, and when the liquid crystal was driven, ultraviolet light of 80 mW was emitted for 60 seconds using a UV irradiation device using a metal halide lamp as a light source. Subsequently, when no voltage was applied, ultraviolet light of 3.5 mW was emitted for 60 minutes using a UV irradiation device using a metal halide lamp as a light source. Finally, the liquid crystal cell was annealed in a clean oven at 120° C. for 10 minutes.

(PSA Process-3)

The liquid crystal cell was annealed in a clean oven at 120° C. for 5 minutes. Next, for the liquid crystal cell, a DC of 0.5 V was applied between the electrodes, and when the liquid crystal was driven, ultraviolet light of 80 mW was emitted for 20 seconds using a UV irradiation device using a metal halide lamp as a light source. Subsequently, a DC of 10 V was applied between the electrodes, and when the liquid crystal was driven, ultraviolet light of 80 mW was emitted for 90 seconds using a UV irradiation device using a metal halide lamp as a light source. Subsequently, when no voltage was applied, ultraviolet light of 3.5 mW was emitted for 90 minutes using a UV irradiation device using a metal halide lamp as a light source. Finally, the liquid crystal cell was annealed in a clean oven at 120° C. for 10 minutes.

(PSA Process-4)

The liquid crystal cell was annealed in a clean oven at 120° C. for 15 minutes. Next, for the liquid crystal cell, a DC of 0.1 V was applied between the electrodes, and when the liquid crystal was driven, ultraviolet light of 80 mW was emitted for 30 seconds using a UV irradiation device using a metal halide lamp as a light source. Subsequently, a DC of 15 V was applied between the electrodes, and when the liquid crystal was driven, ultraviolet light of 80 mW was emitted for 120 seconds using a UV irradiation device using a metal halide lamp as a light source. Subsequently, when no voltage was applied, ultraviolet light of 3.5 mW was emitted for 120 minutes using a UV irradiation device using a metal halide lamp as a light source. Finally, the liquid crystal cell was annealed in a clean oven at 120° C. for 10 minutes.

Based on the above results, it was found that the PSA type liquid crystal display device produced using the liquid crystal composition containing the compound [B] had well-balanced liquid crystal alignment properties (initial alignment), AC afterimage characteristics and DC afterimage characteristics. On the other hand, in Comparative Examples 1 to 3 in which the liquid crystal composition containing no compound [B] was used, DC afterimage characteristics were evaluated as "poor." In addition, in Comparative Example 1, liquid crystal alignment properties and AC afterimage characteristic were evaluated as "poor." In Comparative Example 2, AC afterimage characteristics were evaluated as "acceptable" but liquid crystal alignment properties were evaluated as "poor."

While the present disclosure has been described based on the embodiments, it is understood that the present disclosure is not limited to the above embodiments and structures. The present disclosure includes various modified examples and alternations within the equivalent range. In addition, various combinations and forms, and additionally, other combinations and forms including only one element, or more or fewer of such elements are within the scope and spirit of the present disclosure.

The invention claimed is:
1. A liquid crystal device, comprising:
a pair of substrates each having a conductive film;
a liquid crystal layer which is disposed between the pair of substrates and contains a liquid crystal; and
a liquid crystal control layer which is formed at an interface on a side of the substrate of the liquid crystal layer through polymerization of polymerizable monomers and controls alignment of the liquid crystal,
wherein no liquid crystal alignment film is formed on at least one of the pair of substrates, and
wherein the liquid crystal control layer contains a compound [A] having at least one partial structure selected from the group consisting of an aromatic amino group and a nitrogen-containing aromatic heterocyclic group.
2. The liquid crystal device according to claim 1,
wherein the compound [A] is at least one selected from the group consisting of the following (i) and (ii):
(i) a polymer of a compound including at least one selected from the group consisting of a partial structure derived from a compound represented by the following Formula (1) and a nitrogen-containing aromatic heterocyclic group, and a radically polymerizable group in the same molecule; and
(ii) a compound including at least one selected from the group consisting of a partial structure derived from a compound represented by the following Formula (1), and a nitrogen-containing aromatic heterocyclic group, and at least one group selected from the group consisting of an alkoxysilyl group, a hydroxysilyl group, a hydroxyl group, a carboxyl group or salts thereof, a sulfo group or salts thereof, an amino group, a quaternary ammonium base, a phosphate group or salts thereof, a phosphoric acid ester group, a phosphonium base and a carbamoyl group in the same molecule:

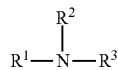

(1)

in Formula (1), $R^1$ is a monovalent aromatic ring group, and $R^2$ and $R^3$ are each independently a hydrogen atom or a monovalent organic group having 1 to 30 carbon atoms, and here, $R^2$ and $R^3$ may be mutually bonded to form a ring structure together with the nitrogen atoms to which $R^2$ and $R^3$ are bonded, and $R^1$ and $R^3$ may be mutually bonded to form a nitrogen-containing condensed ring structure including the nitrogen atoms to which $R^1$ and $R^3$ are bonded in the ring.
3. The liquid crystal device according to claim 1,
wherein the liquid crystal control layer is formed by a liquid crystal composition that contains at least one selected from the group consisting of a polymerization initiator, a photosensitizer and a polymerization inhibitor.
4. The liquid crystal device according to claim 1,
wherein the liquid crystal control layer contains a compound having a partial structure represented by the following Formula (3):

(3)

in Formula (3), $L^1$ is —O—, —CO—, —COO—$*^1$, —OCO—$*^1$, —NX$^5$—, —NX$^5$—CO—$*^1$, —CO—NX$^5$—$*^1$, an alkanediyl group having 1 to 6 carbon atoms, —O—X$^6$—$*^1$, or —X$^6$—O—$*^1$, here, X$^5$ is a hydrogen atom or a monovalent hydrocarbon group having 1 to 10 carbon atoms, and X$^6$ is an alkanediyl group having 1 to 3 carbon atoms, $*^1$ indicates a bond with X$^1$,
X$^1$ and X$^3$ are each independently a single bond, a phenylene group or a cycloalkylene group,
X$^2$ is a single bond, a phenylene group, a cycloalkylene group, —X$^7$—B$^1$—$*^2$, or —B$^1$—$*^2$, or —B$^1$—X$^7$—$*^2$, here, X$^7$ is a phenylene group or a cycloalkylene group, B$^1$ is a single bond, —COO—$*^3$, —OCO—$*^3$, or an alkanediyl group having 1 to 3 carbon atoms, $*^2$ indicates a bond with X$^3$, and $*^3$ indicates a bond with X$^7$,
X$^4$ is a hydrogen atom, a fluorine atom, an alkyl group having 1 to 18 carbon atoms, a fluoroalkyl group having 1 to 18 carbon atoms, an alkoxy group having 1 to 18 carbon atoms, a fluoroalkoxy group having 1 to 18 carbon atoms, or a hydrocarbon group having a steroid structure and having 17 to 51 carbon atoms, and may include a photoinitiator group, here, when X$^4$ is a hydrogen atom, a fluorine atom or has 1 to 3 carbon atoms, not all of X$^1$, X$^2$ and X$^3$ may be a single bond, $*$ indicates a bond.
5. The liquid crystal device according to claim 1,
wherein the liquid crystal has negative dielectric anisotropy.
6. A method for producing a liquid crystal device which includes a pair of substrates each having a conductive film, and in which no liquid crystal alignment film is formed on at least one of the pair of substrates, the method comprising:
step (I) of constituting a liquid crystal cell by disposing the pair of substrates to face each other with a layer of a liquid crystal composition including a liquid crystal and polymerizable monomers therebetween; and
step (II) of emitting light to the liquid crystal cell when a voltage is applied between the conductive films,
wherein the liquid crystal composition contains a compound [B] having at least one partial structure selected from the group consisting of an aromatic amino group and a nitrogen-containing aromatic heterocyclic group.
7. The method for producing a liquid crystal device according to claim 6,
wherein a content of the compound [B] is 0.01 mass % or more and 10 mass % or less with respect to a total amount of the liquid crystal composition.
8. The method for producing a liquid crystal device according to claim 6,
wherein the step (I) is a step in which the liquid crystal composition is applied to one surface of the pair of substrates by ink jet coating, and bonding with the other substrate is then performed to constitute the liquid crystal cell.
9. The method for producing a liquid crystal device according to claim 6,
wherein, before the step (I), a step of applying a silane coupling agent to a surface on which the conductive film is formed on at least one of the pair of substrates is provided.
10. The method for producing a liquid crystal device according to claim 6,
wherein a step of an annealing treatment is provided between the step (I) and the step (II).
11. The method for producing a liquid crystal device according to claim 6, wherein the step (II) includes a first step of emitting light to the liquid crystal cell when a voltage lower than a voltage at which the liquid crystal is driven is applied and a second step of emitting light to the liquid crystal cell when the voltage at which the liquid crystal is driven is applied after the first step.

12. The liquid crystal device according to claim 2, wherein the liquid crystal control layer is formed by a liquid crystal composition that contains at least one selected from the group consisting of a polymerization initiator, a photosensitizer and a polymerization inhibitor.

13. The liquid crystal device according to claim 2, wherein the liquid crystal control layer contains a compound having a partial structure represented by the following Formula (3):

$$*\text{-}L^1\text{-}X^1\text{—}X^2\text{—}X^3\text{—}X^4 \quad (3)$$

in Formula (3), $L^1$ is —O—, —CO—, —COO—$*^1$, —OCO—$*^1$, —NX$^5$—, —NX$^5$—CO—$*^1$, —CO—NX$^5$—$*^1$, an alkanediyl group having 1 to 6 carbon atoms, —O—X$^6$—$*^1$, or —X$^6$—O—$*^1$, here, X$^5$ is a hydrogen atom or a monovalent hydrocarbon group having 1 to 10 carbon atoms, and X$^6$ is an alkanediyl group having 1 to 3 carbon atoms, $*^1$ indicates a bond with X$^1$, X$^1$ and X$^3$ are each independently a single bond, a phenylene group or a cycloalkylene group, X$^2$ is a single bond, a phenylene group, a cycloalkylene group, —X$^7$—B$^1$—$*^2$, or —B$^1$—X$^7$—$*^2$, here, X$^7$ is a phenylene group or a cycloalkylene group, B$^1$ is a single bond, —COO—$*^3$, —OCO—$*^3$, or an alkanediyl group having 1 to 3 carbon atoms, $*^2$ indicates a bond with X$^3$, and $*^3$ indicates a bond with X$^7$, X$^4$ is a hydrogen atom, a fluorine atom, an alkyl group having 1 to 18 carbon atoms, a fluoroalkyl group having 1 to 18 carbon atoms, an alkoxy group having 1 to 18 carbon atoms, a fluoroalkoxy group having 1 to 18 carbon atoms, or a hydrocarbon group having a steroid structure and having 17 to 51 carbon atoms, and may include a photoinitiator group, here, when X$^4$ is a hydrogen atom, a fluorine atom or has 1 to 3 carbon atoms, not all of X$^1$, X$^2$ and X$^3$ may be a single bond, * indicates a bond.

14. The liquid crystal device according to claim 3,
wherein the liquid crystal control layer contains a compound having a partial structure represented by the following Formula (3):

$$*\text{-}L^1\text{-}X^1\text{—}X^2\text{—}X^3\text{—}X^4 \quad (3)$$

in Formula (3), $L^1$ is —O—, —CO—, —COO—$*^1$, —OCO—$*^1$, —NX$^5$—, —NX$^5$—CO—$*^1$, —CO—NX$^5$—$*^1$, an alkanediyl group having 1 to 6 carbon atoms, —O—X$^6$—$*^1$, or —X$^6$—O—$*^1$, here, X$^5$ is a hydrogen atom or a monovalent hydrocarbon group having 1 to 10 carbon atoms, and X$^6$ is an alkanediyl group having 1 to 3 carbon atoms, $*^1$ indicates a bond with X$^1$, X$^1$ and X$^3$ are each independently a single bond, a phenylene group or a cycloalkylene group, X$^2$ is a single bond, a phenylene group, a cycloalkylene group, —X$^7$—B$^1$—$*^2$, or —B$^1$—X$^7$—$*^2$, here, X$^7$ is a phenylene group or a cycloalkylene group, B$^1$ is a single bond, —COO—$*^3$, —OCO—$*^3$, or an alkanediyl group having 1 to 3 carbon atoms, $*^2$ indicates a bond with X$^3$, and $*^3$ indicates a bond with X$^7$, X$^4$ is a hydrogen atom, a fluorine atom, an alkyl group having 1 to 18 carbon atoms, a fluoroalkyl group having 1 to 18 carbon atoms, an alkoxy group having 1 to 18 carbon atoms, a fluoroalkoxy group having 1 to 18 carbon atoms, or a hydrocarbon group having a steroid structure and having 17 to 51 carbon atoms, and may include a photoinitiator group, here, when X$^4$ is a hydrogen atom, a fluorine atom or has 1 to 3 carbon atoms, not all of X$^1$, X$^2$ and X$^3$ may be a single bond, * indicates a bond.

15. The liquid crystal device according to claim 2, wherein the liquid crystal has negative dielectric anisotropy.

16. The liquid crystal device according to claim 3, wherein the liquid crystal has negative dielectric anisotropy.

17. The liquid crystal device according to claim 4, wherein the liquid crystal has negative dielectric anisotropy.

18. The method for producing a liquid crystal device according to claim 7, wherein the step (I) is a step in which the liquid crystal composition is applied to one surface of the pair of substrates by ink jet coating, and bonding with the other substrate is then performed to constitute the liquid crystal cell.

\* \* \* \* \*